US007135625B2

(12) United States Patent
Tanaka et al.

(10) Patent No.: US 7,135,625 B2
(45) Date of Patent: Nov. 14, 2006

(54) GENE CONCERNING BRASSINOSTEROID-SENSITIVITY OF PLANTS AND UTILIZATION THEREOF

(75) Inventors: Hiroshi Tanaka, Ibaraki (JP); Toshiaki Kayano, Ibaraki (JP); Makoto Matsuoka, Aichi (JP)

(73) Assignee: National Institute of Agrobiological Sciences (JP)

( * ) Notice: Subject to any disclaimer, the term of this patent is extended or adjusted under 35 U.S.C. 154(b) by 248 days.

(21) Appl. No.: 10/240,577

(22) PCT Filed: Mar. 30, 2001

(86) PCT No.: PCT/JP01/02770

§ 371 (c)(1),
(2), (4) Date: May 30, 2003

(87) PCT Pub. No.: WO01/73036

PCT Pub. Date: Oct. 4, 2001

(65) Prior Publication Data

US 2004/0088761 A1 May 6, 2004

(30) Foreign Application Priority Data

Mar. 31, 2000 (JP) ............................ 2000-101276

(51) Int. Cl.
*C12N 15/29* (2006.01)
*C12N 15/82* (2006.01)
*C12N 15/87* (2006.01)
*A01H 5/00* (2006.01)
*A01H 5/10* (2006.01)

(52) U.S. Cl. .................. 800/298; 536/23.6; 435/320.1; 435/410

(58) Field of Classification Search ............... 536/23.1, 536/23.6; 435/320.1, 468, 419, 410; 800/278, 800/298, 290, 320

See application file for complete search history.

(56) References Cited

U.S. PATENT DOCUMENTS 6,037,522 A * 3/2000 Dong et al. ................. 800/278

FOREIGN PATENT DOCUMENTS

WO WO 97/35986 * 10/1997

OTHER PUBLICATIONS

Kano-Murakami et al (1993, FEBS 334:365-368).*
Wang et al (2005, Developmental Cell 8:855-865).*
Li, Jianming and Chory, Joanne, "A Putative Leucine-Rich Repeat Receptor Kinase Involved In Brassinosteroid Signal Transduction" *Cell*, Sep. 5, 1997, pp. 929-938, vol. 90.
Yano, Masahiro et al. "*Hd1*, a Major Photoperiod Sensitivity Quantitative Trait Locus in Rice, Is Closely Related to the Arabidopsis Flowering Time Gene CONSTANS" *The Plant Cell*, Dec. 2000, pp. 2473-2483, vol. 12.
Reeck, G.R. et al. "'Homology' in proteins and nucleic acids: A terminology muddle and a way out of it" *Cell*, 1987, 50:667.

* cited by examiner

*Primary Examiner*—Stuart F. Baum
(74) *Attorney, Agent, or Firm*—Saliwanchik, Lloyd & Saliwanchik

(57) ABSTRACT

The present inventors successfully produced rice dwarf mutant d61 and also isolated the OsBRI1 gene which corresponds to a region in the d61 locus. OsBRI1 is found to increase plant brassinosteroid sensitivity. Moreover, the present inventors showed that OsBRI1 functions in growth and development process of rice, such as, internode elongation by inducing internode cell elongation and the inclination of the lamina joint. By introducing antisense nucleotides or dominant negative of OsBRI1, the present inventors produced transgenic rice plants whose phenotype was modified.

10 Claims, 14 Drawing Sheets

```
Rice (T65)   M--DSLWAAIAALFVAAAVVVRGAA-----AADDAQLLEEFRQAVPNQAALKGWSGGDGACRFPGAGCRNGRLTSLSLAGVPLNAEFRAVAATLLQLGS
Arabidopsis  MKTFSSFFLSVTTLFFFSFFSLSFQASPSQSLYREIHQLISFKDVLPDKNLLPDWSSNKNPCTFDGVTCRDDKVTSIDLSSKPLNVGFSAVSSSLLSLTG
                         *1                        *2                   *3

Rice (T65)   VEVLSLRGANVSGALSAAGGARCGSKLQALDLSGNAALRGSVADVAALASACGGLKTLNLSGDAVGAA-KVGGGGGPGFAGLDSLDLSNNKITDDSDLRW
Arabidopsis  LESLFLSNSHINGSVS--GFK-CSASLTSLDLSRNSLSGP-VTTLTSLGSCSG-LKFLNVSSNTLDFPGKVSGGLKLNS--LEVLDLSANSISGANVVGW

Rice (T65)   MV-DAGVGAVRWLDLALNRISG-VPEF---------------------------------------------------------------------TNCSG
Arabidopsis  VLSD-GCGELKHLAISGNKISGDVDVSRCVNLEFLDVSSNNFSTGIPFLGDCSALQHLDISGNKLSGDFSRAISTCTELKLLNISSNQFVGPIPPLPLKS

Rice (T65)   LQYLDLSGNLIVGEVPGGALSDCRGLKVLNLSFNHLAGVFPPDIAGLTSLNALNLSNNNFSGELPGEAFAKLQQLTALSLSFNHFNGSIPDTVASLPE-L
Arabidopsis  LQYLSLAENKFTGEIPDFLSGACDTLTGLDLSGNHFYGAVPPFFGSCSLLESLALSSNNFSGELPMDTLLKMRGLKVLDLSFNEFSGELPESLTNLSASL

Rice (T65)   QQLDLSSNTFSGTIPSSLCQDPNSKLHLLYLQNNYLTGGIPDAVSNCTSLVSLDLSLNYINGSIPASLGDLGNLQDLILWQNELEGEIPASLSRIQGLEH
Arabidopsis  LTLDLSSNNFSGPILPNLCQNPKNTLQELYLQNNGFTGKIPPTLSNCSELVSLHLSFNYLSGTIPSSLGSLSKLRDLKLWLNMLEGEIPQELMYVKTLET

Rice (T65)   LILDYNGLTGSIPPELAKCTKLNWISLASNRLSGPIPSWLGKLSYLAILKLSNNSFSGPIPPELGDCQSLVWLDLNSNQLNGSIPKELAKQSGKMNVGLI
Arabidopsis  LILDFNDLTGEIPSGLSNCTNLNWISLSNNRLTGEIPKWIGRLENLAILKLSNNSFSGNIPAELGDCRSLIWLDLNTNLFNGTIPAAMFKQSGKIAANFI
```

FIG.11

```
Rice (T65)   VGRPYVYLRNDELSSECRGKGSLLEFTSIRPDDLSRMPSKKLCNFT-RMYVGSTEYTFNKNGSMIFLDLSYNQLDSAIPGELGDMFYLMIMNLGHNLLSG
Arabidopsis  AGKRYVYIKNDGMKKECHGAGNLLEFQGIRSEQLNRLSTRNPCNITSRVYGGHTSPTFDNNGSMMFLDMSYNMLSGYIPKEIGSMPYLFILNLGHNDISG

Rice (T65)   TIPSRLAEAKKLAVLDLSYNQLEGPIPNSFSALS-LSEINLSNNQLNGTIPELGSLATFPKSQYENNTGLCGFPLPPCDHSSPRSSNDHQ-SH-RRQASM
Arabidopsis  SIPDEVGDLRGLNILDLSSNKLDGRIPQAMSALTMLTEIDLSNNNLSGPIPEMGQFETFPPAKFLNNPGLCGYPLPRCDPSNADGYAHHQRSHGRRPASL
                                                                                 ========= *4

Rice (T65)   ASSIAMGLLFSLFCIIVIIIAIGSKRRRLKNEEASTSRDIYIDSRSHSATMNSDWRQNLSGTNLLSINLAAFEKPLQNLTLADLVEATNGFHIACQIGSG
Arabidopsis  AGSVAMGLLFSFVCIFGLILVGREMRKRRRKKEAELEMYAEGHGNSGDRTANNTNWKLTGVKEALSINLAAFEKPLRKLTFADLLQATNGFHNDSLIGSG

Rice (T65)   GFGDVYKAQLKDGKVVAIKKLIHVSGQGDREFTAEMETIGKIKHRNLVPLLGYCKAGEERLLVYDYMKFGSLEDVLHDRKKIGKKLNWEARRKIAVGAAR
Arabidopsis  GFGDVYKAILKDGSAVAIKKLIHVSGQGDREFMAEMETIGKIKHRNLVPLLGYCKVGDERLLVYEFMKYGSLEDVLHDPKKAGVKLNWSTRRKIAIGSAR

Rice (T65)   GLAFLHHNCIPHIIHRDMKSSNVLIDEQLEARVSDFGMARLMSVVDTHLSVSTLAGTPGYVPPEYYQSFRCTTKGDVYSYGVVLLELLTGKPPTDSADFG
Arabidopsis  GLAFLHHNCSPHIIHRDMKSSNVLLDENLEARVSDFGMARLMSAMDTHLSVSTLAGTPGYVPPEYYQSFRCSTKGDVYSYGVVLLELLTGKRPTDSPDFG

Rice (T65)   EDNNLVGWVKQHTKLKITDVFDPELLKEDPSVELELLEHLKIACACLDDRPSRRPTMLKVMAMFKEIQAGSTVDSKTSSAAAGSIDEGGYGVLDMPLREA
Arabidopsis  -DNNLVGWVKQHAKLRISDVFDPELMKEDPALEIELLQHLKVAVACLDDRAWRRPTMVQVMAMFKEIQAGSGIDSQSTIRSIEDGGFSTIEMVDMSIKEV

Rice (T65)   KEEKD
Arabidopsis  PEGKL
```

FIG. 14

GENE CONCERNING BRASSINOSTEROID-SENSITIVITY OF PLANTS AND UTILIZATION THEREOF

This application is a National Stage Application of International Application Number PCT/JP01/02770, published, pursuant to PCT Article 21(2).

TECHNICAL FIELD

The present invention relates to a novel gene involved in plant brassinosteroid sensitivity, the protein encoded by the gene, and production and use of the same.

BACKGROUND ART

Research in plant molecular biology has advanced dramatically in recent years and is necessary for the analysis of various physiological phenomena. Dwarfism caused by artificial modification of grass type, especially the control of elongation growth, prevents plants from lodging due to overgrowth caused by over fertilization. This prevention of lodging was demonstrated in Mexican wheat during the "Green Revolution" and in miracle rice (IR-8) developed by the International Rice Research Center. Furthermore, in the case of cultivation at high density, such as rice cultivation, yields are expected to increase as a result of the increase in the amount of sun light each plant receives due to the formation of upright leaves. Moreover, these modifications are very important breeding targets because they may result in yield increases and also increase the efficiency of plant growth maintenance. However, current breeding methods cannot artificially modify plant morphology.

Dwarfism is an abnormal growth caused by mutation in genes involved in controlling normal elongation growth. Plant elongation growth is the result of accumulation of cell division and cell elongation. Cell division and cell elongation are controlled by complex effects caused by various factors, such as, exogenous environmental factors including temperature and light and endogenous environmental factors including plant hormones. Therefore, it is predicted that many genes, such as those related to plant hormone biosynthesis and hormone receptors directly and those related to the control of the expression of these genes, are involved in the dwarfism (Sakamoto et al. (2000) Kagaku to Seibutsu, 38: 131–139).

Almost all modern cultivars of *japonica* rice develop 15–16 phytomers, consisting of leaves, axillary buds, and short or elongated internodes, during the vegetative stage. After the shoot meristem shifts from the vegetative to the reproductive phase, the reproductive meristem develops about 10 phytomers consisting of undeveloped leaf, an elongated internode, and an axillary which develops into the primary rachis branch. The phytomers formed in the vegetative stage can be classified into three types in terms of the morphology of the internode (Suetsugu, Isao. (1968) Japan. J. Crop Sci. 37, 489–498). The first type is developed in the juvenile phase and form undifferentiated nodes and internodes. After the shoot apical meristem (SAM) shifts from the juvenile to the adult phase, the nodal plate of the second type differentiates and the central part of the internode thereof decays to produce an air space. The third type contains long elongated internodes as a result of growth from the intercalary meristem.

Phytomers of type 1 are produced first during vegetative development, followed by type 2 and then type 3 phytomers. Under normal growth conditions, the number of phytomers of each type in many *japonica* cultivars is 4–5, 6–7, and 4–5. The transition from type 1 to type 2 is strictly regulated. After the serial development of 4–5 type 1 phytomers, depending on the cultivar, the SAM develops type 2 phytomers. However, the transition from type 2 to type 3 does not depend on the number of development of type 2 phytomers. The SAM develops 15–16 phytomers and shifts from the vegetative to the reproductive stage, the type 3 phytomers then start to develop, and the uppermost four or five internodes thereof start to elongate. If the timing of the transition is changed by unusual growth conditions, the number of the type 2 phytomers always affected thereby, but the number of the type 3 phytomer with elongated internode is unchanged (Suetsugu, isao. (1968) Japan. J. Crop Sci: 37, 489–498). This indicates that the transition of the SAM from the vegetative to the reproductive phase in rice induces internode elongation, as well as in *Arabidopsis*.

However, there is an important difference between rice and *Arabidopsis*. The elongated internodes in rice are derived from the vegetative SAM while those in *Arabidopsis* come from the reproductive SAM. In rice, the uppermost four or five internodes develop from the vegetative SAM and initially are indistinguishable from the lower type 2 internodes. When the SAM shifts to the reproductive phase, differentiation into type 3 internodes occurs due to the development of intercalary meristems in the internodes. This synchronicity between the phase change of the SAM and the development of the intercalary meristem leads to the possibility that these processes might be linked by a signal coming from the SAM to the uppermost four or five phytomers when its phase change occurs.

A large number of dwarf mutants of rice have been collected and characterized because of their agronomic importance. These dwarf mutants are categorized into six groups based on the elongation pattern of the upper four to five internodes (FIG. 1; redrawn from Takeda, K. (1974) Bull. Fac. Agr. Hirosaki Univ. 22, 19–30. In rice, each internode is numbered from top to bottom such that the uppermost internode just below the panicle is first). The present inventors can see that in the dn-type mutants the length of each internode is almost uniformly reduced, resulting in an elongation pattern similar to that of the wild type plant. In contrast, the dm-type mutants show specific reduction of the second internode. Similar shortening of a specific internode is also observed in the sh- and d6-type mutants, in which only the uppermost first internode or internodes below the uppermost are shortened, respectively. As these mutants with specifically shortened internodes, such as the dm-, d6-, and sh-types, might be defective in the perception of signals coming from the SAM, they should be especially useful for the study of the mechanism of internode elongation and its relationship to changes in the SAM.

Brassinosteroids (BRs) are plant growth-promoting natural products that are required for plant growth and development. There are only a few reports on the physiological effects of brassinosteroids in the growth and development of rice and other plants of the Gramineae family. Physiological researches indicate that exogenous brassinosteroids alone, or in combination with auxin, enhance bending of the lamina joint in rice. The lamina joint has been used for a sensitive bioassay of brassinosteroids (Maeda, E. (1965) Physiol. Plant. 18, 813–827; Wada, K. et al. (1981) Plant and Cell Physiol. 22, 323–325; Takeno, K. and Pharis, R. P. (1982) Plant Cell Physiol. 23, 1275–1281), because of high sensitivity thereof to brassinosteroids. In etiolated wheat seedlings treatment with brassinolide or its derivative, castasterone, stimulates unrolling of the leaf blades (Wada, K. et al.

(1985) Agric. Biol. Chem. 49, 2249–2251). Treatment with low or high concentrations of brassinosteroids promotes or inhibits the growth of roots in rice, respectively (Radi, S. H. and Maeda, E. (1988) J. Crop Sci. 57, 191–198). Brassinosteroids also promote the germination of rice seeds (Yamaguchi, T. et al. (1987) Stimulation of germination in aged rice seeds by pre-treatment with brassinolide. In: Proceeding of the fourteenth annual plant growth regulator society of America Meeting Honolulu. (Cooke A R), pp. 26–27).

Although these results indicate only effects due to exogenous brassinosteroids, not due to endogenous brassinosteroids, they do suggest that endogenous brassinosteroids have an important role in growth and developmental processes in plants of the Gramineae family.

On the other hand, there is some apparent disagreement in the literature as to whether brassinosteroids induce cell elongation in plants of the Gramineae family. That is, brassinolide treatment does not induce elongation of the leaf sheath of rice (Yokota, T. and Takahashi, N. (1986) Chemistry, physiology and agricultural application of brassinolide and related steroids. In: Plant growth substances 1985. (Bopp M, Springer-Verlag, Berlin/Heidelberg/New York) pp.129–138), but it does induce elongation of the coleoptile and mesocotyl in maize (He, R. —Y. et al. (1991) Effects of brassinolide on growth and chilling resistance of maize seedlings. In: Brassinosteroids-Chemistry, Bioactivity and Applications ACS symposium series 474. (Cutler H G C, Yokota T, Adam G, American Chemical Society, Washington D.C.), pp. 220–230).

As shown by brassinosteroids synthesis mutants or brassinosteroids insensitive mutants that show severe dwarfism with abnormal development of organs, the function of brassinolide is known in dicotyledonous plants.

However, little is known about the function of endogenous brassinosteroids in monocotyledonous plants, such as rice or other plants of the Gramineae family.

3. Disclosure of the Invention

The object of the present invention is to provide novel genes involved in brassinosteroid sensitivity from plants, preferably from monocotyledonous plants. Another object of the present invention is to modify plant brassinosteroid sensitivity by controlling the expression of the gene. The modification in plant brassinosteroid sensitivity causes a change in plant morphology. The preferable embodiment of the present invention provides plants with erect leaves which become dwarfed due to the suppression of internode elongation caused by decreased brassinosteroid sensitivity.

By treatment with mutagenesis agent, the present inventors isolated a novel rice dwarf mutant strain d61 (d61-1 and d61-2) which showed lower brassinosteroid sensitivity and had shorter internodes than wild type plants.

Linkage analysis indicated that the d61 locus was highly linked to a gene region that was homologous to *Arabidopsis* BRI1. The present inventors isolated the gene (OsBRI1), which was homologous to *Arabidopsis* BRI1 gene, by screening of a rice genomic DNA library. Nucleotide sequence analysis of the OsBRI1 gene from d61-1 and d61-2 mutants indicated that there were single nucleotide substitutions causing amino acid substitutions at different sites in each d61 allele.

Moreover, in order to confirm that the OsBRI1 gene corresponds to the d61 locus, the OsBRI1 gene was introduced into d61 mutants. As a result, the OsBRI1 gene complimented the d61 phenotype and caused the mutant strain to have a wild-type phenotype. Therefore, it was indicated that d61 mutants are caused by loss of function of the OsBRI1 gene. Phenotypic analysis of plants revealed that the OsBRI1 gene functions in various growth and development processes of rice including internode elongation caused by formation of intercalary meristem and induction of internode cell longitudinal elongation, inclination of the lamina joint, and skotomorphogenesis in the dark.

Moreover, in the case where transgenic rice plants with OsBRI1 antisense nucleotide were produced, most transgenic plants produced erect leaves during seedling growth. All of the transgenic plants showed dwarf phenotype of various levels. Plants transformed with OSBRI1 having the dominant negative phenotype showed the same result.

The present invention had been made in view of such findings, and relates to a novel gene involved in plant brassinosteroid sensitivity, the protein encoded by the gene, and production and use of the same. Moreover, the present invention relates to the production of modified plant by controlling expression of the gene.

More specifically, this invention provides:

(1) a DNA encoding a protein comprising the amino acid sequence of SEQ ID NO: 2;

(2) the DNA of (1), wherein the DNA is a cDNA or a genomic DNA;

(3) the DNA of (1), wherein the DNA comprises a coding region of the nucleotide sequence of SEQ ID NO: 1 or 3;

(4) a DNA encoding a protein which has 55% or more homology to the amino acid sequence of SEQ ID NO: 2 and which is functionally equivalent to a protein comprising the amino acid sequence of SEQ ID NO: 2, the DNA being selected from the group consisting of
  (a) a DNA encoding a protein comprising the amino acid sequence of SEQ ID NO: 2 in which one or more amino acids are substituted, deleted, added, and/or inserted; and
  (b) a DNA hybridizing under stringent conditions with a DNA comprising the nucleotide sequence of SEQ ID NO: 1 or 3;

(5) the DNA of (4), wherein the DNA encodes a protein having a function selected from the group consisting of a function of increasing brassinosteroid sensitivity in a plant, a function of inducing elongation of internode cells of a stem of a plant, a function of positioning microtubules perpendicular to the direction of elongation in an internode of a stem of a plant, a function of suppressing elongation of an internode of a neck of a plant, and a function of increasing inclination of a lamina of a plant;

(6) the DNA of (4) or (5), wherein the DNA is derived from a monocotyledonous plant;

(7) the DNA of (6), wherein the DNA is derived from a plant of the Gramineae family;

(8) a DNA encoding an antisense RNA complementary to a transcript of the DNA of any one of (1) to (7);

(9) a DNA encoding an RNA having ribozyme activity which specifically cleaves a transcript of the DNA of any one of (1) to (7);

(10) a DNA which encodes an RNA repressing expression of the DNA of any one of (1) to (7) due to co-suppression when expressed in a plant cell and which has 90% or more homology to the DNA of any one of (1) to (7);

(11) a DNA which encodes a protein having a dominant negative phenotype to that of a protein encoded by the DNA of any one of (1) to (7);

(12) a vector which comprises the DNA of any one of (1) to (7);

(13) a transformed cell which comprises the DNA of any one of (1) to (7) or the vector of (12);

(14) a protein encoded by the DNA of any one of (1) to (7);

(15) a method for producing the protein of (14) the method comprising the steps of culturing the transformed cell of (13) and recovering an expressed protein from the transformed cell or a culture supernatant thereof;

(16) a vector comprising the DNA of any one of (8) to (11);

(17) a transformed plant cell comprising the DNA of any one of (1) to (11) or the vector of (12) or (16);

(18) a transformed plant comprising the transformed plant cell of (17);

(19) a transformed plant which is a progeny or a clone of the transformed plant of (18);

(20) a breeding material of the transformed plant of (18) or (19); and

(21) an antibody which binds to the protein of (14).

The present invention provides a DNA encoding the OsBRI1 protein derived from rice. The nucleotide sequence of OsBRI1 cDNA is shown in SEQ ID NO: 1, the amino acid sequence of the protein encoded by the DNA is shown in SEQ ID NO: 2, and the nucleotide sequence of the genomic DNA of OsBRI1 is shown in SEQ ID NO: 3 (the genomic DNA of SEQ ID NO: 3 consists of one exon with no intron).

The gene of the present invention causes a rice dwarf mutant (d61) which has short internodes and reduced brassinosteroid sensitivity compared to the wild type. Therefore, it is possible to modify plant morphology by controlling the expression of the OsBRI1 gene.

The preferable modification in plant morphology in the present invention includes dwarfism of plants by suppressing expression of the DNA of the present invention. Dwarfism of plants has great value in agriculture and horticulture. For example, reduction of height of plants can reduce the tendency of plants to lodge and can thereby increase seed weights. Moreover, it is possible to increase the number of plant individuals which can be planted per unit area by reducing height of plants and by making plant shape per plant more compact. These plant modifications have great value specifically in the production of crops such as rice, corn, wheat, and such. It is also possible to produce ornamental plants with new aesthetic value by dwarfism of height or culm length of plants. It is also possible to produce miniature vegetables or fruits with new commercial value, such as "bite-size", by dwarfism of them. Other than for industrial plants, dwarfism is important for experimental plants because, for example, dwarf plants are not only more easily handled but they also help utilize experimental space more effectively by decreasing cultivation space.

It is possible to consider that brassinosteroid sensitivity can be increased in brassinosteroid low sensitive plants by expressing the DNA of the present invention in the plants. Thereby, the yield of whole plants may be increased by growing taller plants. Thus, this will be especially useful for increasing yield for whole feed crops.

DNA encoding the OsBRI1 protein of the present invention includes genomic DNA, cDNA, and chemically synthesized DNA. A genomic DNA and cDNA can be prepared according to conventional methods known to those skilled in the art. More specifically, a genomic DNA can be prepared, for example, as follows: (1) extract genomic DNA from plant cells or tissues; (2) construct a genomic library (utilizing a vector, such as plasmid, phage, cosmid, BAC, PAC, and such); (3) spread the library; and (4) conduct colony hybridization or plaque hybridization using a probe prepared based on the DNA encoding a protein of the present invention (e.g., SEQ ID NO: 1 or 3). Alternatively, a genomic DNA can be prepared by PCR, using primers specific to a DNA encoding the protein of the present invention (e.g. SEQ ID NO: 1 or 3). On the other hand, cDNA can be prepared, for example, as follows: (1) synthesize cDNAs based on mRNAs extracted from plant cells or tissues; (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins functionally equivalent to the OsBRI1 protein of SEQ ID NO: 2. Herein, the term "functionally equivalent to the OsBRI1 protein" means that the object protein has equal functions to those of the OsBRI1 protein of SEQ ID NO: 2, such as, for example, a function of increasing brassinosteroid sensitivity in a plant, a function of inducing elongation of an internode of a stem of a plant, a function of positioning microtubules perpendicular to the direction of elongation in internode cells of a stem of a plant, a function of suppressing elongation of an internode of a neck of a plant, and/or a function of increasing inclination of a lamina of a plant. Such DNA is derived preferably from monocotyledonous plants, more preferably from plants of the Gramineae family, and most preferably from rice.

Examples of such DNAs include those encoding mutants, derivatives, alleles, variants, and homologues comprising the amino acid sequence of SEQ ID NO: 2 wherein one or more amino acids are substituted, deleted, added, and/or inserted.

Examples of methods for preparing a DNA encoding a protein comprising altered amino acids well known to those skilled in the art include the site-directed mutagenesis (Kramer, W. and Fritz, H. -J. (1987) "Oligonucleotide-directed construction of mutagenesis via gapped duplex DNA." Methods in Enzymology, 154: 350–367). The amino acid sequence of a protein may also be mutated in nature due to the mutation of a nucleotide sequence. A DNA encoding proteins having the amino acid sequence of a natural OsBRI1 protein (SEQ ID NO: 2) wherein one or more amino acids are substituted, deleted, and/or added are also included in the DNA of the present invention, so long as they encode a protein functionally equivalent to the natural OsBRI1 protein. Additionally, nucleotide sequence mutants that do not give rise to amino acid sequence changes in the protein (degeneracy mutants) are also included in the DNA of the present invention. The number of nucleotide mutations of the DNA of interest corresponds to, at amino acid level, typically 100 residues or less, preferably 50 residues or less, more preferably 20 residues or less, and still more preferably 10 residues or less (for example, 5 residues or less, or 3 residues or less).

Whether a certain DNA actually encodes a protein which has a function of increasing inclination of a lamina of a plant can be evaluated, for example, by performing a "lamina joint test" for plants in which the expression of the DNA has been suppressed and by comparing the results with those for wild-type plants (See Example 4). The result of the test may also be an index for evaluating brassinosteroid sensitivity in a plant. In order to evaluate whether the DNA encodes a protein which has a function of inducing elongation of an internode of a stem of a plant, a function of positioning microtubules perpendicular to the direction of elongation in internode cells of a stem of a plant, or a function of suppressing elongation of an internode of a neck of a plant, the morphology of the internode cell of the plant in which expression of the DNA has been suppressed can be observed to be compared with that of wild type (See Examples 2 and 3).

A DNA encoding a protein functionally equivalent to the OsBRI1 protein described in SEQ ID NO: 2 can be produced, for example, by methods well known to those skilled in the art including: methods using hybridization techniques (Southern, E. M. (1975) Journal of Molecular Biology, 98, 503); and polymerase chain reaction (PCR) techniques (Saiki, R. K. et al. (1985) Science, 230, 1350–1354; Saiki, R. K. et al. (1988) Science, 239, 487–491). That is, it is routine for a person skilled in the art to isolate a DNA with high homology to the OsBRI1 gene from rice and other plants using the OsBRI1 gene (SEQ ID NO: 1 or 3) or parts thereof as a probe, and oligonucleotides hybridizing specifically to the gene as a primer. Such DNA encoding proteins functionally equivalent to the OsBRI1 protein, obtainable by hybridization techniques or PCR techniques, are included in the DNA of this invention.

Hybridization reactions to isolate such DNAs are preferably conducted under stringent conditions. Stringent hybridization conditions of the present invention include conditions such as: 6 M urea, 0.4% SDS, and 0.5×SSC; and those which yield a similar stringency with the conditions. DNAs with higher homology are expected to be isolated efficiently when hybridization is performed under conditions with higher stringency, for example, 6 M urea, 0.4% SDS, and 0.1×SSC. Those DNAs isolated under such conditions are expected to encode a protein having a high amino acid level homology with OsBRI1 protein (SEQ ID NO: 2). Herein, "high homology" means an identity of at least 55% or more, more preferably 70% or more, and most preferably 90% or more (e.g., 95% or more), between full-length of amino acids.

The degree of homology of one amino acid sequence or nucleotide sequence to another can be determined by following the algorithm BLAST by Karlin and Altschul (Proc. Natl. Acad. Sci. USA, 90: 5873–5877, 1993). Programs such as BLASTN and BLASTX were developed based on this algorithm (Altschul et al. J. Mol. Biol. 215: 403–410, 1990). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art.

The DNA of the present invention can be used, for example, to prepare recombinant proteins, produce transformed plants with phenotypes altered by controlling expression thereof as described above, and so on.

A recombinant protein is usually prepared by inserting a DNA encoding a protein of the present invention into an appropriate expression vector, introducing said vector into an appropriate cell, culturing the transformed cells, and purifying expressed proteins.

A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells besides the above described *E. coli.* A vector can be introduced into a host cell by a variety of methods known to one skilled in the art. For example, a transformation method using calcium ions (Mandel, M. and Higa, A. (1970) Journal of Molecular Biology, 53, 158–162; Hanahan, D. (1983) Journal of Molecular Biology, 166, 557–580) can be used to introduce a vector into *E. coli.* A recombinant protein expressed in host cells can be purified and recovered from the host cells or the culture supernatant thereof by known methods. When a recombinant protein is expressed as a fusion protein with maltose binding protein or other partners, the recombinant protein can be easily purified by affinity chromatography.

The resulting protein can be used to prepare an antibody that binds to the protein. For example, a polyclonal antibody can be prepared by immunizing immune animals, such as rabbits, with a purified protein of the present invention or its portion, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the cell. The obtained antibody can be utilized to purify or detect a protein of the present invention. Accordingly, the present invention includes antibodies that bind to proteins of the invention.

In order to produce a transformed plant in which DNAs of the present invention are expressed, a DNA encoding a protein of the present invention is inserted into an appropriate vector; the vector is then introduced into a plant cell; and finally, the resulting transformed plant cell is regenerated.

On the other hand, a transformed plant with suppressed expression of DNAs of the present invention can be created using DNA that represses the expression of a DNA encoding a protein of the present invention: wherein the DNA is inserted into an appropriate vector, the vector is introduced into a plant cell, and then, the resulting transformed plant cell is regenerated. The phrase "suppression of expression of DNA encoding a protein of the present invention" includes suppression of gene transcription as well as suppression of translation into protein. It also includes not only the complete inability of expression of DNA but also reduction of expression.

The expression of a specific endogenous gene in plants can be repressed by methods utilizing antisense technology, the methods which are commonly used in the art. Ecker et al. were the first to demonstrate the antisense effect of an antisense RNA introduced by electroporation in plant cells by using the transient gene expression method (J. R. Ecker and R. W. Davis (1986) Proc. Natl. Acad. Sci. USA 83: 5372). Thereafter, the target gene expression was reportedly reduced in tobacco and petunias by expressing antisense RNAs (A. R. van der Krol et al. (1988) Nature 333: 866). The antisense technique has now been established as a means to repress target gene expression in plants.

Multiple factors are required for antisense nucleic acid to repress the target gene expression. These include, inhibition of transcription initiation by triple strand formation; suppression of transcription by hybrid formation at the site where the RNA polymerase has formed a local open loop structure; transcription inhibition by hybrid formation with the RNA being synthesized; suppression of splicing by hybrid formation at the junction between an intron and an exon; suppression of splicing by hybrid formation at the site of spliceosome formation; suppression of mRNA translocation from the nucleus to the cytoplasm by hybrid formation with mRNA; suppression of splicing by hybrid formation at the capping site or at the poly A addition site; suppression of translation initiation by hybrid formation at the binding site for the translation initiation factors; suppression of translation by hybrid formation at the site for ribosome binding near the initiation codon; inhibition of peptide chain elongation by hybrid formation in the translated region or at the polysome binding sites of mRNA; and suppression of gene expression by hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)", Nihon Seikagakukai Hen (The Japanese Biochemical Society), Tokyo Kagaku Dozin, pp. 319–347, (1993)).

An antisense sequence of the present invention can repress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention includes DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary so long as it can effectively inhibit the gene expression. The transcribed RNA is preferably at least 90%, and most preferably at least 95% complementary to the transcribed products of the target gene. Sequence complementarity may be determined using the above-described search.

In order to effectively inhibit the expression of the target gene by means of an antisense sequence, the antisense DNA should be at least 15 nucleotides long, preferably at least 100 nucleotides long, and more preferably at least 500 nucleotides long. The antisense DNA to be used is generally shorter than 5 kb, and preferably shorter than 2.5 kb.

DNA encoding ribozymes can also be used to repress the expression of endogenous genes. A ribozyme is an RNA molecule that has catalytic activity. There are many ribozymes having various activities. Research on ribozymes as RNA cleaving enzymes has enabled the design of a ribozyme that site-specifically cleaves RNA. While some ribozymes of the group I intron type or the mRNA contained in RNaseP consist of 400 nucleotides or more, others belonging to the hammerhead type or the hairpin type have an activity domain of about 40 nucleotides (Makoto Koizumi and Eiko Ohtsuka, (1990) Tanpakushitsu Kakusan Kohso (Nucleic acid, Protein, and Enzyme), 35: 2191).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M.. Koizumi et al., (1988) FEBS Lett. 228: 225). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al., (1988) FEBS Lett. 239: 285; Makoto Koizumi and Eiko Ohtsuka, (1990) Tanpakushitsu Kakusan Kohso (Protein, Nucleic acid, and Enzyme), 35: 2191; M. Koizumi et al., (1989) Nucleic Acids Res. 17: 7059). For example, in the coding region of the OsBRI1 gene (SEQ ID NO: 1 or 3), there is a plurality of sites that can be used as the ribozyme target.

The hairpin type ribozyme is also useful in the present invention. A hairpin type ribozyme can be found, for example, in the minus strand of the satellite RNA of tobacco ringspot virus (J. M. Buzayan, Nature 323: 349 (1986)). This ribozyme has also been shown to target-specifically cleave RNA (Y. Kikuchi and N. Sasaki, (1992) Nucleic Acids Res. 19: 6751; Yo Kikuchi, (1992) Kagaku To Seibutsu (Chemistry and Biology) 30: 112).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al. (1992) Biochem. Biophys. Res. Commun. 186: 1271). By using such ribozymes, it is possible to specifically cleave the transcripts of the target gene in the present invention, thereby repressing the expression of said gene.

Endogenous gene expression can also be repressed by co-suppression through the transformation by DNA having a sequence identical or similar to the target gene sequence. "Co-suppression" refers to the phenomenon in which, when a gene having a sequence identical or similar to the target endogenous gene sequence is introduced into plants by transformation, expression of both the introduced exogenous gene and the target endogenous gene becomes repressed. Although the detailed mechanism of co-suppression is unknown, it is frequently observed in plants (Curr. Biol. (1996) 7: R793 (1997), Curr. Biol. 6: 810). For example, if one wishes to obtain a plant body in which the OsBRI1 gene is co-repressed, the plant in question can be transformed with a vector DNA designed so as to express the OsBRI1 gene or DNA having a similar sequence to select a plant having the OsBRI1 mutant character, e.g., a plant with suppressed internode elongation, among the resultant plants. The gene to be used for co-suppression does not need to be completely identical to the target gene, but it should have at least 70% or more sequence identity, preferably 80% or more sequence identity, and more preferably 90% or more (e.g., 95% or more) sequence identity. Sequence identity may be determined by above-described search.

In addition, endogenous gene expression in the present invention can also be repressed by transforming the plant with a gene having the dominant negative phenotype of the target gene. Herein, "a DNA encoding the protein having the dominant negative phenotype" refers to a DNA encoding a protein which, when the DNA is expressed, can eliminate or reduce the activity of the protein encoded by the endogenous gene of the present invention inherent to the plant. Preferably, it is a DNA encoding the peptide (e.g., peptide which contains from 739 to 1035 residues of amino acids of SEQ ID NO: 2 or peptides of another protein equivalent to the peptide) which lacks the N-terminal region but contains the kinase region of the protein of the present invention. Whether the DNA of interest has the function to eliminate or enhance activity of the endogenous gene of the present invention can be determined, as mentioned above, by whether the DNA of interest eliminates or reduces a function of increasing brassinosteroid sensitivity in a plant, a function of inducing elongation of an internode of a stem of a plant, a function of positioning microtubules perpendicular to the direction of elongation in internode cells of a stem of a plant, a function of suppressing elongation of an internode of a neck of a plant, and/or a function of increasing inclination of a lamina of a plant.

Vectors used for the transformation of plant cells are not limited as long as the vector can express inserted genes in plant cells. For example, vectors comprising promoters for constitutive gene expression in plant cells (e.g., califlower mosaic virus 35S promoter); and promoters inducible by exogenous stimuli can be used. The term "plant cell" used herein includes various forms of plant cells, such as cultured cell suspensions, protoplasts, leaf sections, and callus.

A vector can be introduced into plant cells by known methods, such as the polyethylene glycol method, electroporation, *Agrobacterium* mediated transfer, and particle bombardment. Plants can be regenerated from transformed plant cells by known methods depending on the type of the plant cell (Toki et al., (1995) Plant Physiol. 100:1503–1507). For example, transformation and regeneration methods for rice plants include: (1) introducing genes into protoplasts using polyethylene glycol, and regenerating the plant body (suitable for indica rice cultivars) (Datta, S. K. (1995) in "Gene Transfer To Plants", Potrykus I and Spangenberg Eds., pp66–74); (2) introducing genes into protoplasts using electric pulse, and regenerating the plant body (suitable for japonica rice cultivars) (Toki et al (1992) Plant Physiol. 100, 1503–1507); (3) introducing genes directly into cells by the particle bombardment, and regenerating the plant body (Christou et al. (1991) Bio/Technology, 9: 957–962); (4) introducing genes using *Agrobacterium*, and regenerating the plant body; and so on. These methods are already established in the art and are widely used in the technical field of the present invention. Such methods can be suitably used for the present invention.

Once a transformed plant, wherein the DNA of the present invention is introduced into the genome, is obtained, it is possible to gain descendants from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as descendants or clones thereof. Plant cells transformed with the DNA of the present invention, plant bodies including these cells, descendants and clones of the plant, as well as breeding materials obtained from the plant, its descendant and clones, are all included in the present invention.

The plant of the present invention is preferably a monocotyledonous plant, more preferably a plant of the Gramineae family, and most preferably a rice. The phenotype of the plant of the present invention is different from the wild type phenotype. The phenotypes changed in the plants developed by the present invention include brassinosteroid sensitivity of a plant, plant growth such as internode cell elongation of the plant stem and internode elongation of the ear, inclination of leaves, and the positioning of microtubules perpendicular to the direction of internode cell elongation in the plant stem.

(A) Gross morphology. (Left) Wild type plant; (centre) d61-1 mutant (weak allele); (right) d61-2 mutant (strong allele).

(B) Elongation pattern of internodes. The wild type plant (left) shows the N-type of the elongation pattern, while the d61-1 (centre) and d61-2 (right) mutants show typical dn- and d6-type patterns, respectively.

(C) Panicle structure. The wild type plant (left) has a short panicle, while the d61-1 (centre) and d61-2 (right) mutants have longer panicles.

(D) Erect leaf of d61. The leaves of the wild type plant (left) are bent at the lamina joint indicated by the white arrow, while the leaves of d61-1 (centre) and d61-2 (right) mutants are more erect.

(E) Leaf sheath of d61. The leaf sheath in the d61-1 (centre) and d61-2 (right) mutants is shorter than in the wild type plants (left).

Figure 3:
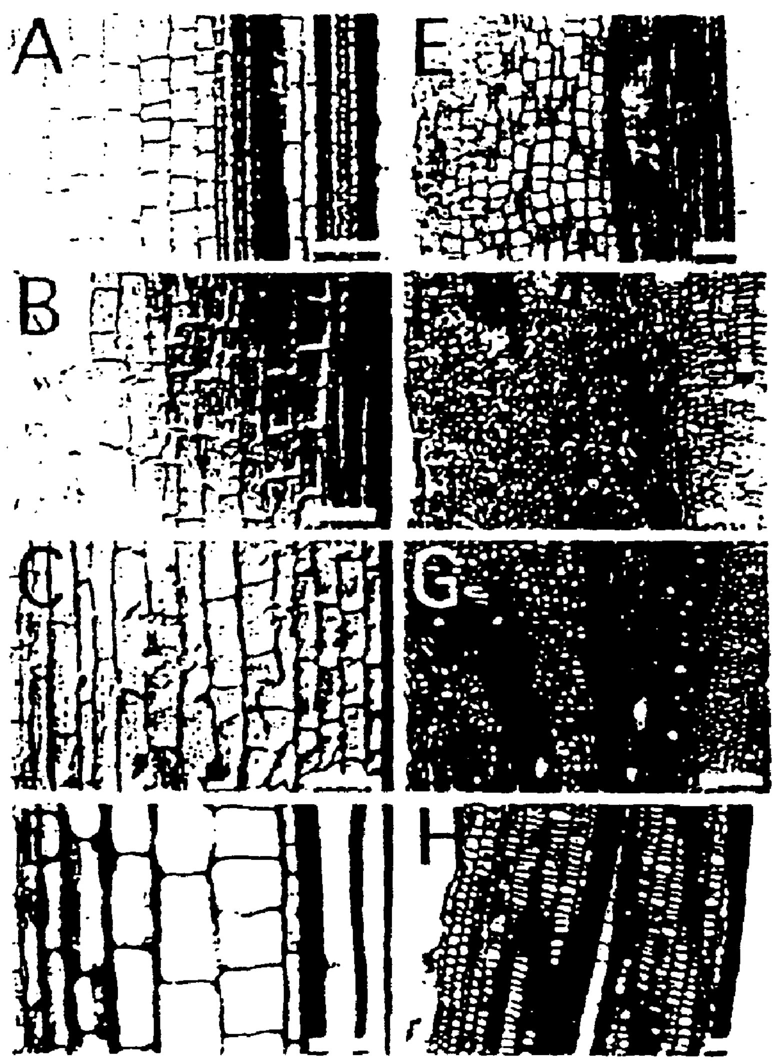

FIG. 3 represents microphotographs which show the structure of well-developed internodes from wild type and d61-2 rice plants, as follows:

(A) longitudinal sections of the first internodes from wild type;

(B) longitudinal sections of the second internodes from wild type;

(C) longitudinal sections of the third internodes from wild type;

(D) longitudinal sections of the fourth internodes from wild type;

(E) longitudinal sections of the first internodes from d61-2 rice plants;

(F) longitudinal sections of the second internodes from d61-2 rice plants;

(G) longitudinal sections of the third internodes from d61-2 rice plants; and (H) longitudinal sections of the fourth internodes from d61-2 rice plants.

Bar=100 μm, respectively.

Figure 4:
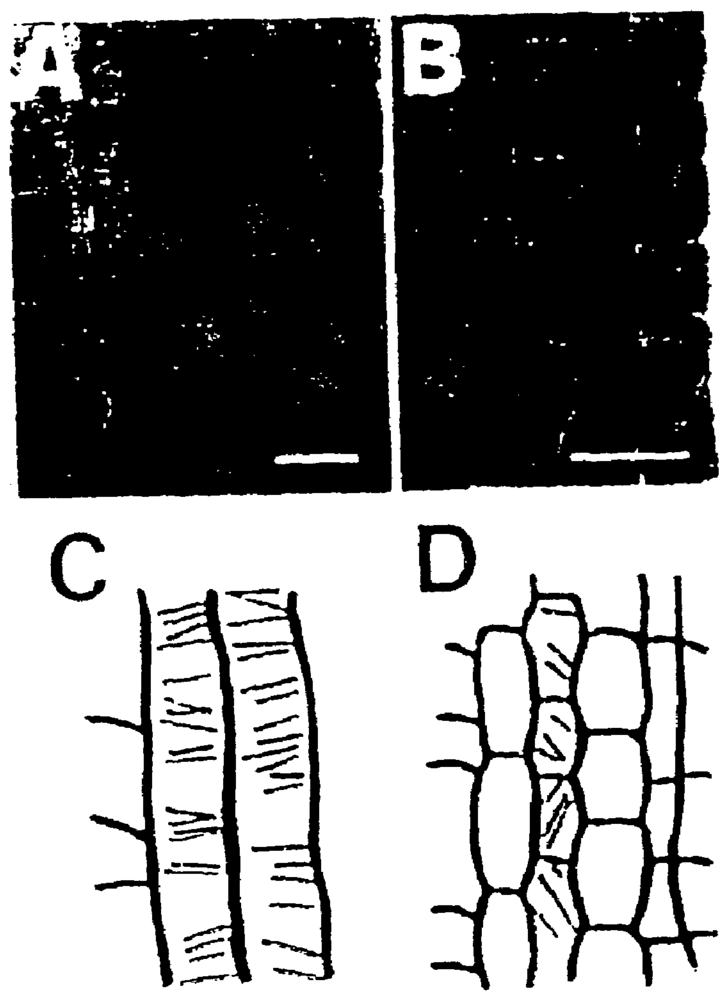

FIG. 4 are photographs and drawings which show the orientation of microtubules in elongating sells in the first internode of wild type and d61-2 plants, consisting of immunofluorescence images (A and B) or schematic presentation (C and D) of the microtubule arrangement in internodal parenchyma cells of the first internode from wild type (A and C) and d61-2 (B and D) plants. Bars=50 μm.

Figure 5:
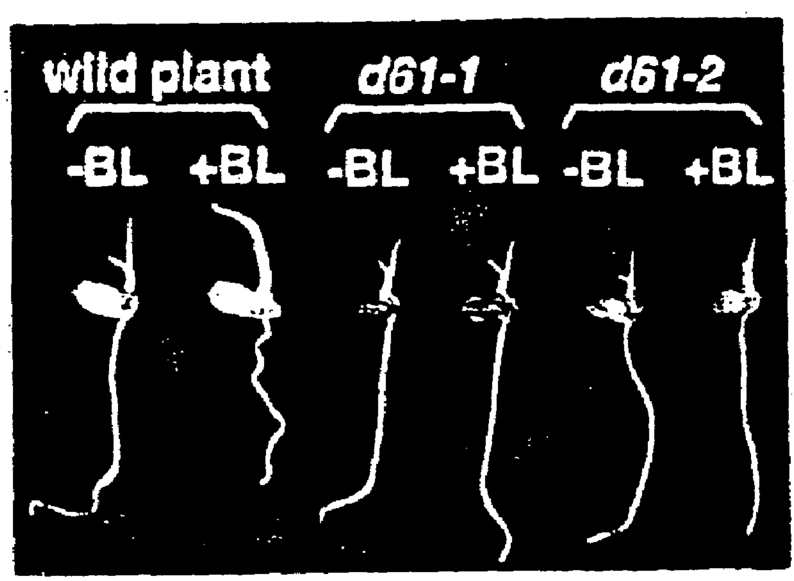

FIG. 5 is a photograph which shows the response of seedlings of wild plant, D61-1, and d61-2 to brassinolide. Seeds were germinated on agar plates in the presence or absence of 1 μM brassinolide (BL). Seedlings were observed 1 day after germination. BL treatment induced abnormal growth in wild plant, while mutant seedlings were not affected thereto.

Figure 6:
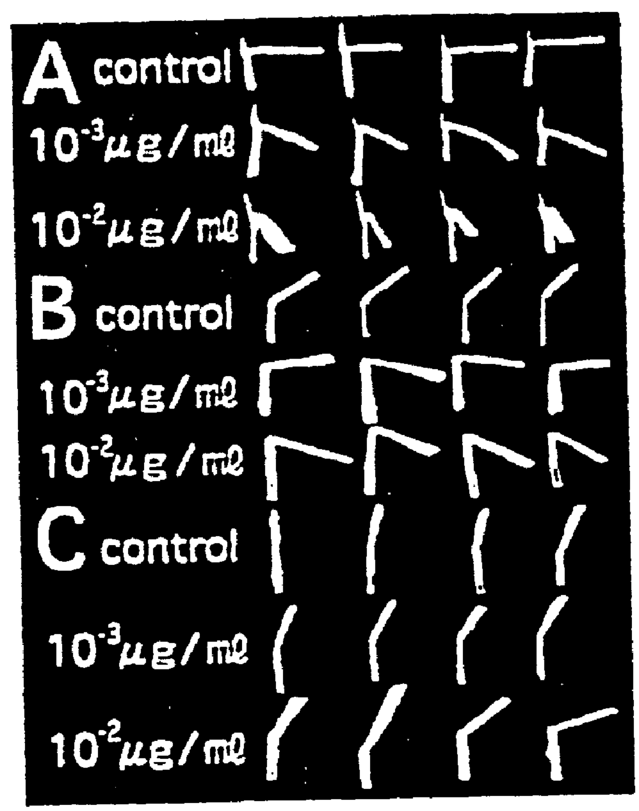

FIG. 6 is a photograph which shows effect of brassinolide on the degree of inclination of etiolated leaf lamina in wild type, d61-1, and d61-2 plants.

The highest response of the leaf from wild type (panel A) and reduced response in mutant plants d61-1 (panel B) and d61-2 (panel C) are shown.

Figure 7:
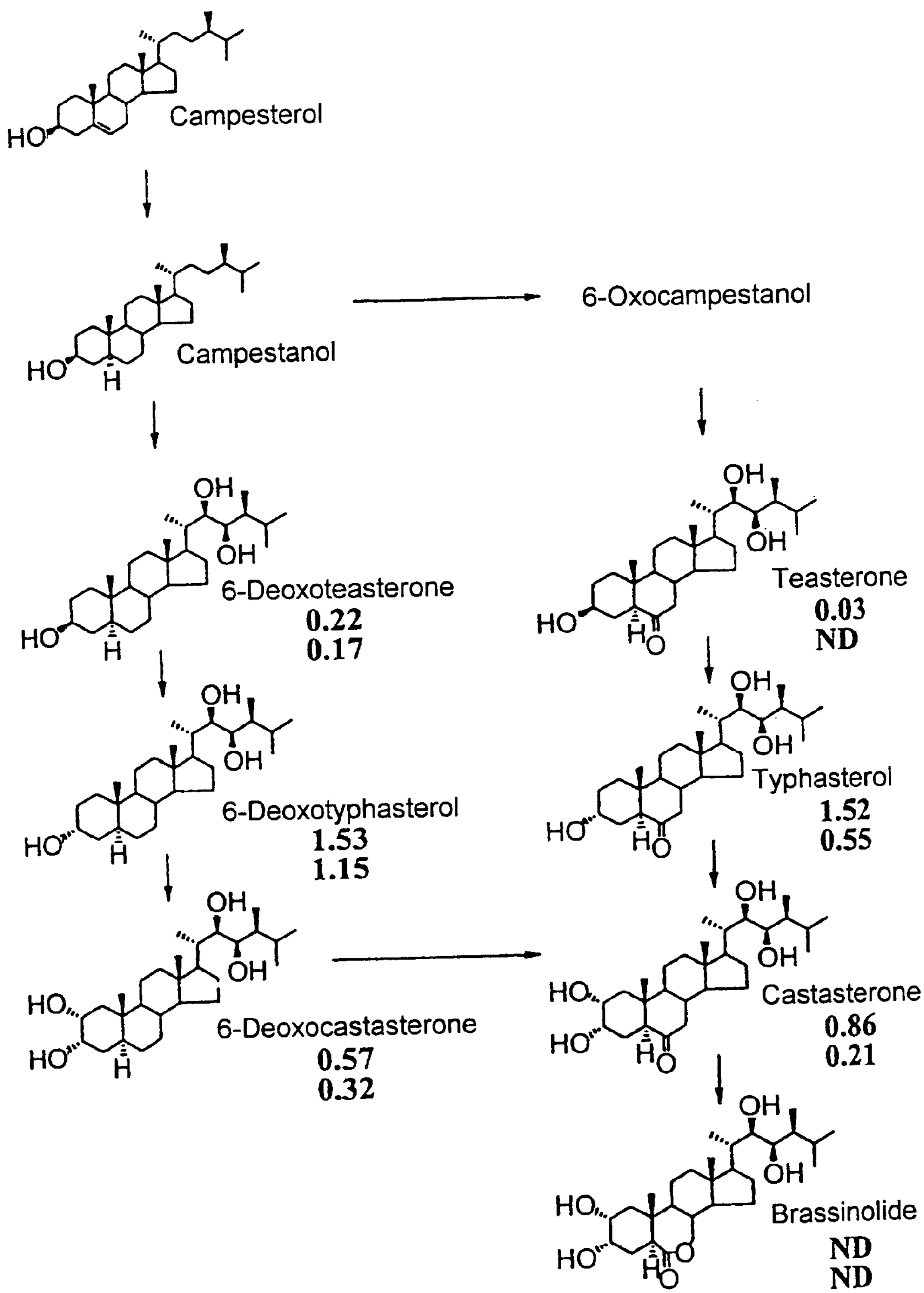

FIG. 7 is a drawing which shows amounts of brassinosteroids in wild type and d61-2 rice plants, and biosynthetic precursors thereof.

The amounts (ng/g fresh weight) of each compound in mutant (upper) and wild type (lower) plants are shown. ND indicates not detected.

Figure 8:
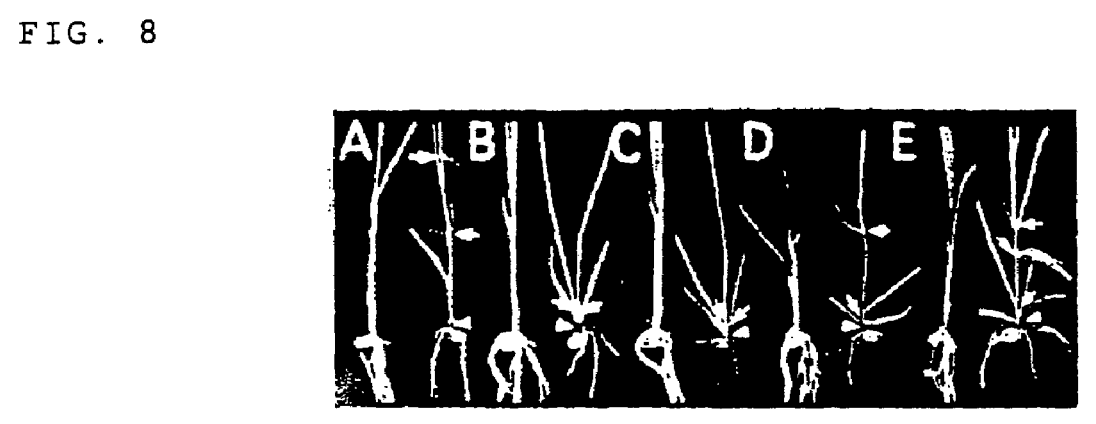

FIG. 8 is a photograph which shows de-etiolation phenotype of the d61 in the dark.

(A) Wild Type

Left: seedlings grown for two weeks in the dark

Right: seedlings grown for two weeks in the light

The internode elongation in wild type (A) and two gibberellin deficient rice mutants, d18 (D) and d35 (E), are indicated in the dark.

(B) d61-1 mutant

Left: seedlings grown for two weeks in the dark

Right: seedlings grown for two weeks in the light

The white arrows indicate internode elongations in right of each panel, the dark condition. No elongation was observed in the light (left of each panel).

(C) d61-2 mutant

Left: seedlings grown for two weeks in the dark

Right: seedlings grown for two weeks in the light

No internode elongation in d61 mutant, d61-1 (B) and d61-2 (C), is observed even in the dark. The present inventors stripped the leaf sheath of plants grown in the dark.

(D) d18 mutant

Left: seedlings grown for two weeks in the dark

Right: seedlings grown for two weeks in the light (E) d35 mutant

Left: seedlings grown for two weeks in the dark

Right: seedlings grown for two weeks in the light

Figure 9:
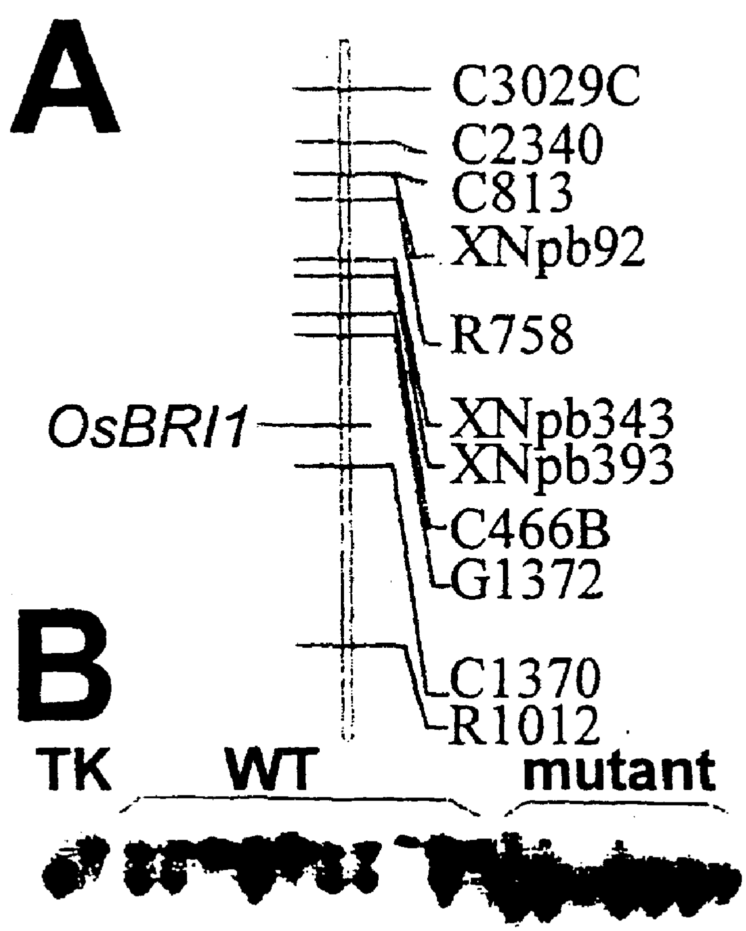

FIG. 9 provides a drawing and photograph that show the strong linkage between the d61 locus and OsBRI1.

(A) is a drawing that indicates map position of the d61 locus on the long arm of chromosome 1.

(B) is a photograph that indicates the result of DNA hybridization analysis to test the linkage between the d61 locus and OsBRI1. The RFLP of OsBRI1 was observed between *Japonica* parent T65 (lane T, 12.5 kb), and the *Indica* parent Kasarath (lane K, 17.5 kb) when the genomic DNAs were digested with EcoRI. Plants with a normal phenotype (WT) were heterozygous (12.5+17.5 k.b) or homozygous for the *Indica* allele (17.5 kb), while the plants with the mutant phenotype (mutant) were always homozygous for the *Japonica* allele (12.5 kb).

FIG. 10 shows a comparison of the deduced amino acid sequences of OsBRI1 (SEQ ID NO: 2 and *Arabidopsis* BRI1 (SEQ ID NO: 6). Identical residues are boxed. The underlined regions, * 1, *2, *3, and *4, indicate: a putative signal peptide, a leucine zipper motif, N, and C sides of a cysteine pair.

FIG. 11 is a continuation of FIG. 10.

Figure 12:
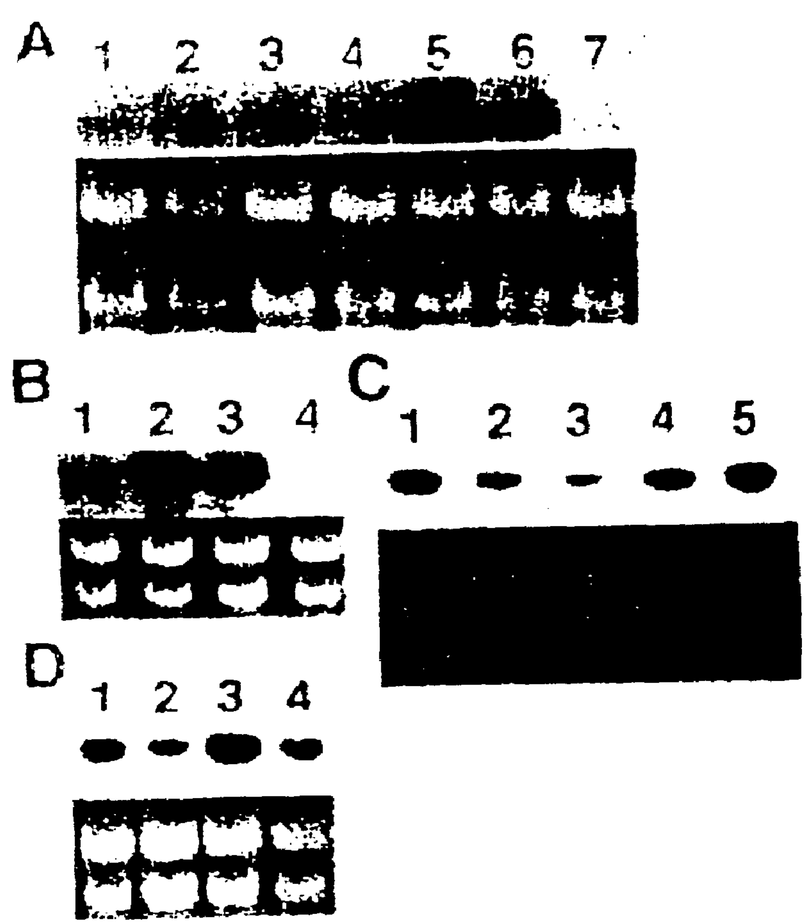

FIG. 12 is a photograph which shows expression pattern of OsBRI1 in various organs.

Total RNA (10 μg) from various organs of wild type plants were loaded into each lane.

Organ specific expression of OsBRI1

(A) Leaf blade (lane 1), leaf sheath (lane 2), developed flower (lane 3), rachis (lane 4), shoot apex (lane 5), root (lane 6), and seed (lane 7).

Region Specific Expression of OsBRI1 in the Developing First Internode (B) Node (lane 1), divisional zone (lane 2), elongation zone (lane 3, and elongated zone (lane 4) in developing internodes.

Differential Expression of OsBRI1 in Each Elongating Internode (C) The divisional and elongation zones of the first to fourth internodes, respectively, at the actively elongating stage for each internode (lanes 1–4). OsBRI1 was expressed at a high level also in the unelongated stem at the vegetative phase (lane 5).

Light-dependent and Brassinolide-dependent Expression of OsBRI1

(D) Rice seedlings were grown for ten days in the light (lanes 1 and 2) or dark (lane 3 and 4) on agar plate in the presence (lane 2 and 4) or absence (lane 1 and 3) of 1 μM brassinolide.

Figure 13:
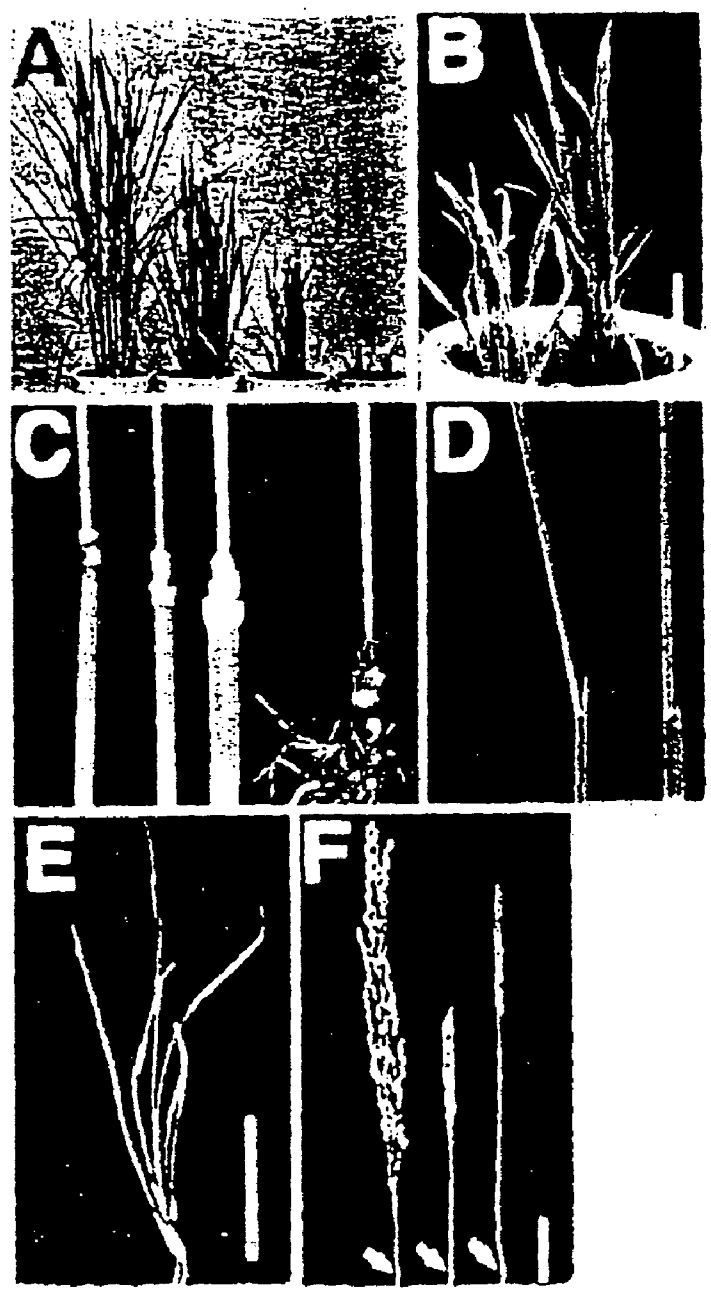

FIG. 13 is a photograph which shows phenotype of the transgenic rice plants expressing the antisense strand of OsBRI1.

(A) Dwarf phenotype of OsBRI1 antisense plants with intermediate (centre) and severe phenotypes (right) compared to a wild type plant (left).

(B) Close up view of a transgenic plant with severe phenotype.

Bar=5 cm.

(C) Naked culm internodes of a transgenic plant. From left to right, wild type plant with normal elongation pattern of internodes and transgenic plants with the dm, dm-d6, and d6 phenotypes are shown, respectively.

(D) Leaf morphology of wild type (left) and transgenic plants with mild phenotype (right), showing the erect leaves in the latter.

(E) Abnormal leaf morphology of a transgenic plant with a severe phenotype, showing lack of developed sheath organs. Bar=10 cm.

(F) Panicle morphology in wild type (left) and transgenic plants with the mild (centre) and intermediate (right) phenotypes FIG. 14 is a photograph which shows the phenotype of a transgenic plant that expresses dominant negative of OsBRI1. The transgenic plant (left) and a control plant containing vector without any inserts (right) are shown.

BEST MODE FOR CARRYING OUT THE INVENTION

The present invention is specifically illustrated below with reference to Examples, but it is not to be construed as being limited thereto.

Rice (*Oriza sativa*) seeds were soaked in distilled water and made to imbibe for 48 h at 30° C. After washing the seeds with distilled water several times, the seeds were germinated in a dark chamber at 30° C. for 8 days. Rice plants were grown in the field or in the greenhouse at 30° C. (day) and 24° C. (night).

EXAMPLE 1

Characterization of Rice d61 Dwarf Mutants

Figure 1:
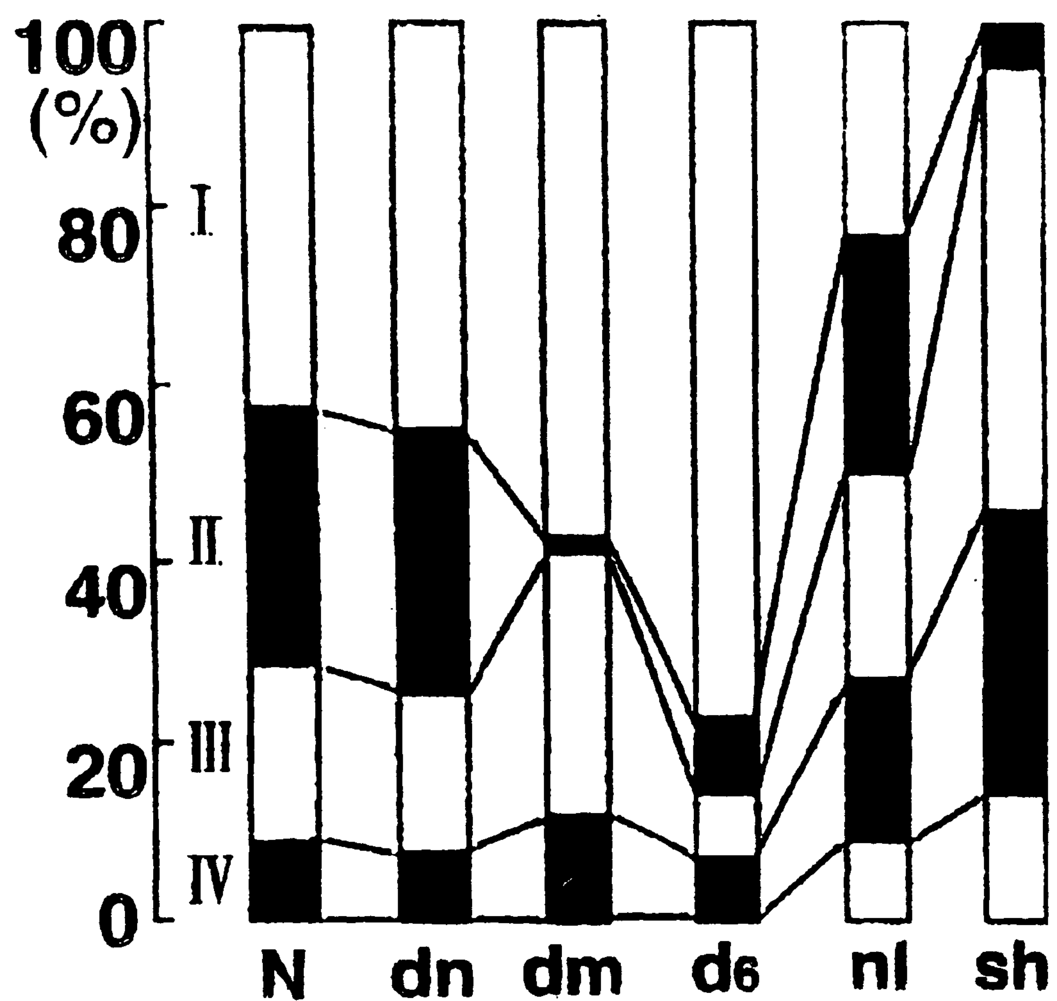
FIG. 1 shows a schematic diagram of the internode elongation pattern of wild type rice and various dwarf mutant and wild-type rice plants. The relative lengths of the each internode to the stem are shown in the schematic diagram. Wild type is shown as N.
Figure 2:
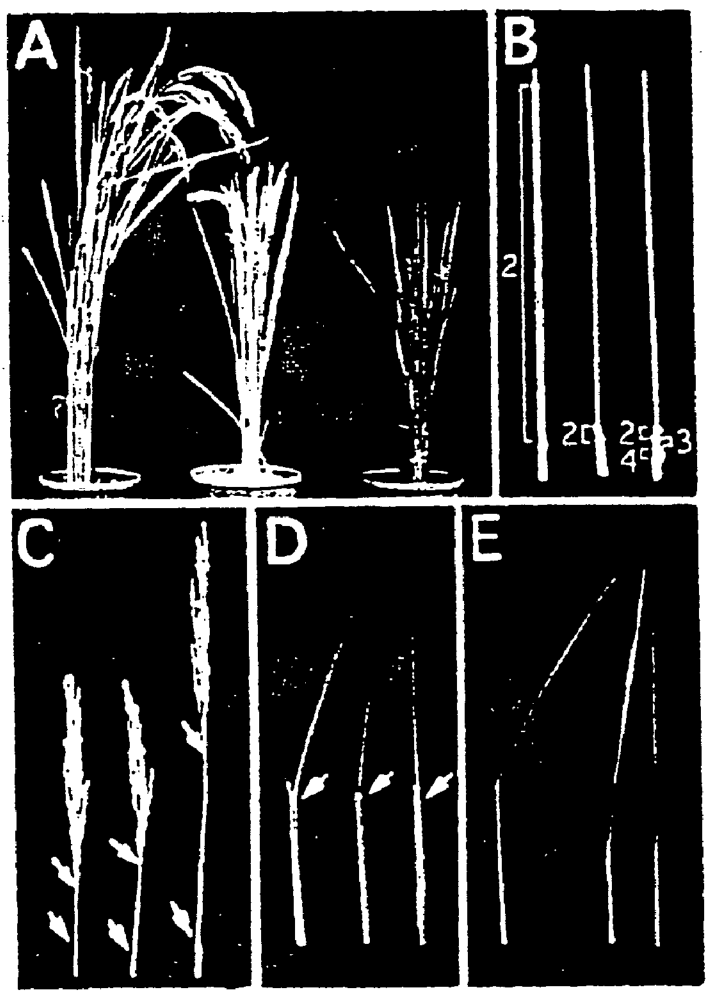
FIG. 2 represents photographs which show the phenotype of the d61 mutants.

Rice dwarf mutants d61-1 and d61-2 were obtained by treatment with N-methyl-N-nitrosourea (NMU), respectively (FIG. 2A).

d61 mutants carrying the weak allele specifically fail to elongate the second internode (dm-type), while those with the strong allele fail to elongate all of the internodes except the uppermost one (d6-type) (Wu, X. et al. (1999) Bread. Sci. 49, 147–153).

The culm of d61-2 is much shorter than that of d61-1. In addition, d61-1 shows typical dm-type pattern of internode elongation, while d61-2 shows the d6-type (FIG. 2B). Thus, they were initially characterized as two independent mutants. However, crossing test demonstrated that they are alleles on a single locus. This is the first example of rice mutants of a single locus which show different, specific patterns of inhibition of internode elongation.

These mutants have other abnormal phenotypes as a result of pleiotropic effect, as well as that inhibiting internode elongation specifically. For example, the neck internode of the mutants is longer than that of wild type plants (FIG. 2C). As the neck internode length shows an inverse relationship to the length of culm in these plants, wild type plant thus has the longest culm and shortest neck internode, the d61-1 mutant has intermediate length culm and neck internodes, and d61-2 has the shortest culm and the longest neck internode.

Another abnormal phenotype of these mutants is erect leaves (FIG. 2D). In wild type plants, the leaf blade bends away from the vertical axis of the leaf sheath towards the abaxial side. The leaf blade bends away from the leaf sheath at a specific organ, lamina joint, which is indicated by arrows in FIG. 2D. When the leaf blades and sheaths are fully elongated, cells at the adaxial side of the lamina joint start to elongate causing the leaf blade to bend away form the leaf sheath. However, the leaf blade of a mutant does not clearly bend away from the leaf sheath. In the d61-1 mutant some leaves still show slight bending (FIG. 2D, centre), but in the d61-2 mutant almost all the leaves are completely erect (FIG. 2D, right).

That is, the degree of lamina inclination correlates to the severity of the dwarfism. The continuity of the severity in lamina inclination suggests that the longitudinal elongation of the surface cells on the adaxial side of lamina, which causes the lamina inclination, responds continuously to the brassinosteroid signal.

The lack of bending of the mutant leaves is not caused by none or less development of the lamina joint. Indeed, even the d61-2 mutant with the severe phenotype in lamina joint developed normally. The mutants showed shorter leaf sheaths than that of the wild type plants (FIG. 2E).

EXAMPLE 2

Observation of Cell Morphology in Internode

Internode elongation is caused by cell division in the intercalary meristem and cell elongation in the elongation zone (Hoshikawa, K. (1989) Stem. In: The growing rice plant. (Nobunkyo), pp. 123–148). Therefore, dwarfing of the culms could be due to a defect in one or both of these processes. To distinguish between these possibilities, the present inventors examined sections of each internode from adult plants under the microscope.

Developing or developed culms at various stages were fixed in FAA (formalin: glacial acetic acid: 70% ethanol, 1:1:18), and dehydrated in a graded ethanol series. The samples were embedded in a Technovit 7100 resin (Kurzer, Germany) polymerized at 45° C. and 3–5 μm sections were cut, stained with Toluidine Blue and observed under the light microscope.

FIG. 3 shows the cell morphology of the upper four internodes in a wild type plant and the d61-2 mutant. In the wild type plant, cells in all internodes were longitudinally elongated and well organized with longitudinal files (FIGS. 3A, 3B, 3C, and 3D). Similar longitudinal cell files were also seen in the first internodes of the mutant plants, although the cells were a little shorter than those in the wild type plant (FIG. 3E). In the non-elongated internodes of the mutant, such as the second and third internodes, the arrangement of cells was disorganized with no organized cell files apparent (FIGS. 3F and 3G). Disorganization of the internodal cells indicates that the intercalary meristems of the mutants, which normally give rise to the longitudinal files of elongated cells, are not developed in the non-elongated internodes. In the fourth internode, organized cell files were present but the cells were much shorter than that of the wild type plant (compare FIGS. 3D and 3H). This suggests that intercalary meristems did develop in these internodes but the cells failed to elongate.

EXAMPLE 3

Observation of the Arrangement of Microtubules

It was described in detail that cell elongation depends on the orientation of microfibrils (Ledbetter, M. C. and Porter, K. R. (1963) J. Cell Biol. 19, 239–250; Green, P. B. (1962) Science. 138, 1404). Therefore, the present inventors examined the arrangement of microtubules in the internodal cells of wild type and d61-2 mutant plants by immunofluorescence microscopy.

Microtubules in internodal parenchyma tissue were strained immunofluorescently. More specifically, internodal parenchyma tissue was prefixed for 45 min at room temperature in 3.7% (w/v) paraformaldehyde in microtubule-stabilizing buffer (0.1 M piperazine-diethanolsulphonic acid, 1 mM $MgCl_2$, 5 mM ethyleneglycol-bis (3-aminomethylether-N,N,N',N'-tetraacetic acid, 0.2% (v/v) Triton X-100, 1% (w/v) glycerol, pH 6.9). Longitudinal sections were cut with a fresh razor blade, collected in the fixation solution, treated for 40 min therein, and washed in the fixation solution without paraformaldehyde. The sections were then incubated with a rabbit anti-α-tubulin monoclonal antibody, diluted 1:500 in phosphate-buffered saline containing 0.1% (v/v) Triton X-100, for 1 h at 37° C. The sections were washed three times in the buffer without anti-serum and then incubated overnight at 4° C. with fluorescein-isothiocyanate-labeled mouse anti-rabbit IgG antibody diluted 1:50 in phosphate-buffered saline containing 0.1% (v/v) Triton X-100. After three washes in the same buffer, they were mounted in antifading solution (Fluoro Guard Antifade reagent, Bio-Rad) and observed under a fluorescence microscope.

As a result, in wild type plants, the microtubules in cells of elongating internodes were arranged in an orderly manner at right angles to the direction of elongation (FIG. 4A). However, in the d61-2 mutant, the microtubules in cells of the first elongating internode were arranged in different directions in each cell, apparently at random (FIG. 4B). In addition, the microtubules in the mutant appeared to be thinner and less distinct relative to those of the wild type plant.

Moreover, the present inventors were unable to observe any organized microtubule arrangement in cells from non-elongated internodes of the mutant plants.

Taken together with the results in Example 2 show that non-elongated internodes in the mutants fail to develop an intercalary meristem and the cells lack an organized arrangement of microtubules. In those internodes that do elongate in the mutants, although less than in the wild type plants, an intercalary meristem does develop but the cells lack a well-organized microtubule arrangement.

EXAMPLE 4

Test of the Sensitivity against Brassinosteroids

The dwarf phenotype and erect leaves of the d61 mutant suggests the possibility that the D61 gene product could be involved in either the biosynthesis or signal transduction of brassinosteroids. Thus, the present inventors carried out the following experiments.

First, the present inventors attempted to restore the dwarfism of the d61 mutants, but could not be achieved it by the application of brassinolide.

Next, seeds of the wild type and mutant plants were germinated on agar plates with or without 1 μM brassinolide. The characteristics of whole seedlings were observed 1 day after germination.

The result showed that, when the wild-type plants were germinated on the plates with brassinolide, the coleoptiles of wild type plants elongated abnormally resulting in a twisted shape and the foliage leaves grew poorly and did not break through the coleoptile (FIG. 5). Furthermore, root elongation was inhibited and thus the roots were not straight but developed in a wavy form. The wild type plants grew normally in the absence of brassinolide, with coleoptile elongation stopping at an early stage of germination and then foliage leaves elongating to break out of the coleoptile. Roots developed normally and did not have any wavy form (FIG. 5). In contrast to the wild type plants, the mutants showed normal growth patterns, as well as that of the wild type plants on plates without brassinosteroids, even in the presence of brassinosteroids. These results suggest that the mutant plants are less sensitive to brassinolide than the wild type plants.

The present inventors further tested the sensitivity of the mutants to brassinolide using a more quantitative method.

The degree of bending between the leaf blade and leaf sheath in rice is well known to be sensitive to the concentration of brassinolide or its related compounds. This unusual character of rice leaf is the basis for a quantitative bioassay for brassinosteroids, known as the lamina joint test (Wada, Ketal. (1981) Plant and Cell Physiol. 22, 323–325), even though the biological function of endogenous brassinosteroids in monocotyledonous plants including rice remains unknown. If the mutants are less sensitive to brassinosteroids, the degree of bending between the leaf blade and sheath of the mutant plants will be less than that of the wild type plants.

Lamina joints of first leave of wild type T65 plant (the background strain of the mutants), d61-1 mutant, and d61-2 mutant were tested with $10^{-3}$ and $10^{-2}$ μg/ml of brassinosteroids, respectively.

As a result, the leaf blade of wild type T65 plants was bent almost at right angles to the axis of the leaf sheath in the absence of exogenous brassinolide becoming even more bent in the presence of increasing concentrations of brassinolide (FIG. 6A). When the mutants were used for the test, the degree of bending increased with higher concentrations of brassinolide as in the wild type plants. However, the absolute degree of bending of the leaves from the mutants was much less than that of the wild type plants under the same conditions (FIGS. 6B and C). This was particularly evident with the d61-2 mutant in which control leaves were almost straight and leaves treated with $10^{-2}$ μg/ml brassinolide were bent at less than a right angle to the leaf sheath axis. The results of the lamina joint test confirm that the sensitivity of the mutants to brassinosteroids is less than that of the wild type plants.

EXAMPLE 5

Quantitative Analysis of Brassinosteroids in the d61-2 Mutant

Example 4 demonstrates that the mutants have reduced sensitivity to brassinosteroids. That is, mutants may synthesize higher concentrations of brassinosteroids to compensate for the reduction. Thus, the present inventors measured the concentration of brassinosteroids in both the d61-2 mutant and wild type plants using GC-SIM with internal standards.

Wild type and d61-2 plants were grown in a greenhouse with a 16-hrs day and 8-hrs night. Shoots from 2-month old plants were harvested and then immediately lyophilized. Lyophilized shoots (50 g fresh weight equivalent) were extracted twice with 250 ml of MeOH—$CHCl_3$ (4:1 [v/v]), and deuterium-labeled internal standards (1 ng/g fresh weight) were added thereto. The extract was partitioned between $CHCl_3$ and $H_2O$ after evaporation of the solvent in vacuo. The $CHCl_3$-soluble fraction was subjected to silica gel chromatography (Wako-gel C-300; Wako; 15 g). The column was sequentially eluted with 150 ml each of $CHCl_3$ containing 2% methanol and $CHCl_3$ containing 7% methanol. Each fraction was purified by Sephadex LH-20 column chromatography, where the column volume was 200 ml and the column was eluted with methanol-$CHCl_3$ (4:1 [v/v]). The fractions eluting from 0.6 to 0.8 ($V_e/V_t$) were collected as brassinosteroid fractions. After pre-purification on an ODS cartridge column (10×50 mm [internal diameter×column length]) in MeOH, the eluates derived from 7% MeOH fractions were subjected to ODS-HPLC at a flow rate of 8 ml/min with 65% acetonitrile as the solvent. In HPLC purification, the 7% methanol eluate was resolved into castasterone (retention time from 10 to 15 min), typhasterol (25 to 30 min), 6-deoxocastasterone (40 to 45 min) fractions, and the 2% methanol eluate gave a 6-deoxotyphasterol fraction (55 to 60 min). Each fraction was derivatized and analyzed by GC-SIM. The endogenous levels of brassinosteroids were calculated from the ratio of the peak areas of the prominent ions from the endogenous brassinosteroids and the internal standard.

As a result, brassinosteroid was not detected in shoots from either the mutant or wild type plants, suggesting that brassinolide is a minor component of the total brassinosteroids pool. However, all of the other brassinosteroids were detected in both plant types, with the exception of teasterone which was not found in the wild type plants. The contents of all of the brassinosteroid compounds detected were greater in the mutant plants (FIG. 7). In particular, castasterone was four times higher in the mutant than in the wild plant. These results support the hypothesis that the mutants have no sensitivity to brassinosteroids.

EXAMPLE 6

De-etiolation Phenotype of the d61 Mutants

Reduction of hypocotyl elongation and emergence of opening of the cotyledons and primary leaves in complete darkness are reported in *Arabidopsis* mutants with deficiencies in brassinosteroid biosynthesis or brassinosteroid signaling when grown in the dark (Kauschmann, A et al. (1996) Plant J. 9, 701–703; Szekeres, M. et al. (1996) Cell. 85, 171–182).

This de-etiolated (DET) or constitutive photomorphogenesis (COP) phenotype in darkness is a common feature of *Arabidopsis* brassinosteroids-related mutants. A similar DET or COP phenotype is also observed in a tomato dwarf (d) mutant that shows a short hypocotyl, lack of apical hook, and expansion of cotyledons (Bishop, G. J. et al. (1996) Plant Cell. 8, 959–969). In contrast, a pea brassinosteroids-defective mutant, 1 kb, does not show such a DET phenotype (Nomura, T. et al. (1997) Plant Physiol. 93, 572–577). Mutants were grown in the dark to determine whether such DET or COP phenotypes were also found in monocotyledonous plants and whether the d61 rice mutants showed characteristics of skotomorphogenesis.

As a result, when wild type plants were germinated in the dark, they showed unusual elongation of the mesocotyl and internodes compared to light-grown seedlings (FIG. 8A). Such elongation of the mesocotyl and internodes did not occur in the mutants even in the dark (FIGS. 8B and 8C). This failure of the mesocotyl and internodes to elongate in the dark is not a common characteristic of rice dwarf mutants. For example, two other dwarf mutants, d18 and d35, which are deficient in gibberellin biosynthesis, showed elongated mesocotyls and internodes when grown in the dark (FIGS. 8D and 8E, respectively).

Thus, it is conceivable that the reduced elongation of the mesocotyl and internodes are specific feature of the d61 mutants and that the d61 mutants have de-etiolated phenotype. In addition, it is also indicated that de-etiolation due to defects in brassinosteroid signal is common characteristic in both dicotyledonous and monocotyledonous plants. That is, it is conceivable that brassinosteroid signals are important for skotomorphogenesis in both dicotyledonous and monocotyledonous plants.

EXAMPLE 7

Mapping and Linkage Analysis of D61 Locus

For mapping of the D61 locus, the present inventors crossed the d61-2 mutant with an *Indica* rice cultivar, Kasarath (*Oriza sativa L.* cv. *Kasarath*). The linkage analysis between the mutant phenotype and restriction fragment polymorphism (RFLP) markers released from the Rice Genome Project (Tsukuba, Japan) revealed that the D61 locus maps to the long arm of chromosome 1, with tight linkage to the RFLP marker, C1370 (FIG. 9A).

As d61 could be characterized as a mutant with no or reduced sensitivity to brassinosteroid, the present inventors also tested the linkage between the mutant phenotype and a rice gene that is homologous to the *Arabidopsis* BRI1 gene.

The *Arabidopsis* BRI1 gene was isolated as the only gene that is involved in brassinosteroid signal transduction (Li, J. and Chory, J. (1997) Cell. 90, 929–938). Furthermore, the present inventors carried out a BLAST search to identify one rice EST clone, S1676, with high homology to the *Arabidopsis* BRI1 gene (Li, J. and Chory, J. (1997) Cell. 90, 929–938).

Rice genomic DNA was isolated from leaf tissue using an ISOPLANT DNA isolation kit (Nippon GENE Co., Japan). One μg of the genomic DNA was digested with appropriate restriction enzymes and transferred onto Hybond N+ membranes (Amersham) under alkaline conditions. The membrane was probed using the partial cDNA fragment (corresponding to the region from Ser 740 to Asp 1116 in the kinase domain), which specifically hybridized with the genomic DNA fragment encoding OsBRI1. All of the steps were carried out according to the method described by Church and Gilbert (1984) PNAS. 81, 1991–1995, except that membranes were hybridized at high stringency (68° C.).

An RFLP between the *Japonica* (12.5 kb) and *Indica* (17.5 kb) rice was observed when genomic DNAs were digested with EcoRI and probed with the cDNA clone. All F2 plants with the mutant phenotype were homozygous for the *Japonica* allele (12.5 kb), whereas the F2 plants with the wild type phenotype were either homozygous for the *Indica* allele (17.5 kb) or heterozygous with both the *Japonica* and *Indica* alleles (12.5+17.5 kb, FIG. 9B). This result demonstrates that the D61 locus is closely linked to the position of the rice gene that is homologous to the *Arabidopsis* BRI1.

EXAMPLE 8

Identification of the d61 Gene

The above linkage analysis strongly suggested that the d61 mutation is caused by loss of function of the rice homologue of the *Arabidopsis* BRI1 gene. To test this possibility, the present inventors screened rice genomic DNA library with probes and isolated the entire length. of the rice BRI1 homologous gene (OsBRI1, *Oryza sativa* BRI1). Hybridization in this screening was performed as described in Church and Gilbert (1984) except that membranes were hybridized at higher stringency (68° C.). Sequencing was carried out according to the same method described by Church and Gilbert.

The structure of the OsBRI1 gene is quite similar to the *Arabidopsis* BRI1 gene in its entire length (FIG. 10 and FIG. 11). The predicted OsBRI1 polypeptide contains several domains that are also present in the BRI1, and the functions of which were discussed (Li, J. and Chory, J. (1997) Cell. 90, 929–938). These domains consist of a putative signal peptide, two conservatively spaced cysteine pairs, a leucine-rich repeat domain, a transmembrane domain, and a kinase domain. The N-terminus of the predicted OsBRI1 polypeptide has a hydrophobic segment which is predicted to act as a signal peptide to transport the protein to the plasma membrane. In the BRI1 protein, Li and Chory predicted a potential 4-hepted amphipathic leucine zipper motif following the signal peptide (Li, J. and Chory, J. (1997) Cell. 90, 929–938), but OsBRI1 does not have such a typical leucine zipper motif in the corresponding region.

A putative extracellular domain (from $Met^1$ to $Leu^{670}$), consisting of 22 tandem copies of a leucine-rich repeat (LRR) of about 24-amino acids with 12 potential N-glycosylation sites (Asn-X-Ser/Thr), is flanked by pairs of conservatively spaced cysteines. The LRR has been implicated to function in protein—protein interactions (Kobe, B. and Deisenhofer, J. (1994) Trends Biochem. Science. 19, 415–421).

In comparison to the BRI1 sequence, OsBRI1 lacks three LRR domains corresponding to the third to fifth repeat of the *Arabidopsis* BRI1. The two LRRs before this deletion are less conserved except for the consensus residues found between other LRR proteins, but the LRRs of both proteins are well conserved after the deletion in both the LRR consensus residues and non-conservative amino acids. An unusual feature of the LRR region of BRI1 is the presence of a 70-amino acid island between the 21st and 22nd LRR (Li, J. and Chory, J. (1997) Cell. 90, 929–938). A highly similar feature is also present in OsBRI1 with the same number of amino acids between the 18th and 19th LRRs corresponding to the site of island in BRI1. This unusual amino acid island in LRR region must be important for functions thereof, because exchange of an amino acid residue in this island resulted in the loss of function of BRI1 (Li, J. and Chory, J. (1997) Cell. 90, 929–938) This motif was thought to be important for direct interaction with brassinosteroids or for maintaining the structure of the brassinosteroids-binding domain (Li, J. and Chory, J. (1997) Cell. 90, 929–938).

The protein kinase domain of OsBRI1 has all eleven conserved subdomains of eukaryotic protein kinases, retaining the invariant amino acid residues in their proper positions (Hanks, S. K. and Quinn, A. M. (1991) Meth. Enzymol. 200, 38–62). The protein kinase domain of OsBRI1 is highly related to that of BRI1 (44%) over the entire region. It is also related to the kinase domains of other receptor-like protein kinases in higher plants such as ERECTA (Torii, K. U. et al. (1996) Plant Cell. 8, 735–746), CLV1 (Clark, S. E. et al. (1997) Cell. 3, 575–585), and RLK5 (Walker, J. C. (1993) Plant J. 3, 451–456) from *Arabidopsis*, and Xa21 from rice (Song et al., 1995). The highly conserved structure of OsBRI1 and these receptor-like protein kinases, especially in subdomains VIb and VIII, suggests that OsBRI1 is a serine/threonine kinase rather than a tyrosine kinase (Hanks, S. K. and Quinn, A. M. (1991) Meth. Enzymol. 200, 38–62).

EXAMPLE 9

Sequencing of OsBRI1 Gene in d61-1 and d61-2 Mutants

The present inventors also determined the entire sequences of the OsBRI1 gene in the d61-1 and d61-2 mutants, and compared them to that of the wild type plant. The present inventors identified a single nucleotide substitution in each mutant allele at different sites (Table 1). The genomic mutation in d61-1 resulted in exchange from threonine to isoleucine at residue 989 in subdomain IX of the kinase domain which is conserved between OsBRI1 and BRI1. The genomic mutation in d61-2 changed valine to methionine at residue 491 in the 17th LRR, just before the unusual 70-amino acid interrupting region. These mutations in the OsBRI1 genes from the d61 mutants provide strong evidence that OsBRI1 encodes the D61 locus.

TABLE 1

| Alleles | Characteristics of mutation | Position of coding sequence |
|---|---|---|
| d61-1 | C → T | Thr → Ile (989) |
| d61-2 | G → A | Val → Met (491) |

EXAMPLE 10

Molecular Complementation Analysis of the d61 Mutation by the Introduction of OsBRI1 Gene To confirm that OsBRI1 corresponds to the d61 locus, the present inventors carried out complementation analysis of the d61-1 mutant by introduction of the wild-type OsBRI1 gene.

More specifically, to confirm complementarity of d61 phenotype due to introduction of a genomic OsBRI1 clone including its 5' and 3' flanking regions, a 10.5-kb restriction fragment including the entire coding region was cloned into the XbaI-SmaI sites of the hygromycin resistance binary vector pBI101-Hm3 (Sato, Y. et al. (1999) EMBO J. 18, 992–1002). pBI-cont was used as a control vector. The present inventors performed rice tissue culture and *Agrobacterium tumefaciens* mediated transformation.

Transformation of d61 with a control vector that carries no rice genomic DNA had no apparent effect on the culm length or the structure of leaves. However, when a 10.5 kb DNA fragment containing the entire wild-type OsBRI1 gene was introduced, the normal phenotype was recovered in almost plants that were resistant to hygromycin. This result confirms that the d61 mutant phenotype is caused by the loss-of-function mutation in the OsBRI1 gene.

EXAMPLE 11

RNA Hybridization Analysis of OsBRI1

Nothing is known about the function of endogenous brassinosteroids in monocotyledonous plants. Therefore, the present inventors tested the expression pattern of the OsBRI1 gene in various rice organs by RNA hybridization analysis.

RNA was isolated from various rice tissues as described in literature (Chomczynski, P. and Sacchi, N.: Anal. Biochem. (1987) 162:156). Ten μg of total RNA were electrophoresed in a 1% agarose gel, then transferred to a Hybond $N^+$ membrane (Amersham), and analyzed by RNA gel blot hybridization. The present inventors used a partial cDNA fragment ($Ser^{740}$ to $Asp^{1116}$ corresponding to the kinase domain), as a probe which specifically hybridized to the genomic DNA fragment encoding OsBRI1. DNA hybridization analysis was performed with the same probe and hybridization conditions as described above.

As a result, a single, strongly-hybridizing band was detected in RNA from vegetative shoot apices (FIG. 12A). The size of the band was approximately 3.5 kb, which is almost the same size as the longest cDNA clone. More weakly-hybridizing bands of the same size were also observed in RNA from flowers, rachis, roots, and expanded leaf sheaths, while no or very faint bands were observed in RNA from expanded leaf blades. Thus, the expression of OsBRI1 varies markedly between organs suggesting that the sensitivity to brassinosteroids also differs among these organs.

The present inventors also examined the expression of OsBRI1 in elongating culms (FIG. 12B). Elongating culms were divided into four parts: the node and the division, elongation, and elongated zones of the internode. As a result, the most strongly hybridizing band was found in RNA from the division zone. RNA from the elongation zone also gave a strong signal. RNA from the node gave only a weak signal, whilst that from the elongated internode gave no signal at all. These results indicate that the elongating culm has different sensitivities to brassinosteroids partially, with the most sensitive parts being the division and elongation zones where cells are actively dividing and elongating.

The present inventors further examined the expression of OsBRI1 in the elongation zones of the upper four internodes at the stage when each internode was actively elongating. A strongly hybridizing band was found in RNA from the elongation zone of the uppermost (first) and the lowest (fourth) internodes, while relatively weak bands were seen with the second and third internodes (FIG. 12C). This result indicates that the internodes differ in their sensitivity to brassinosteroids, with the second and third internodes being the least sensitive.

It was observed that the internodes differ in their sensitivity to brassinosteroids. It suggests that the uppermost and fourth internodes have higher sensitivity to brassinosteroids than the second and third internodes, if the amount of OsBRI1 is a limiting factor in brassinosteroid signal transduction. This idea is supported by the mutant allele with the intermediate, dm-d6 type phenotype. These plants show specific reduction of the second and third internodes while the uppermost and fourth internodes are elongated. This is consistent with the second and third internodes, with lower expression level of OsBRI1, having lower sensitivity to brassinosteroids such that they are unable to respond to the brassinosteroid signal and elongate. Presumably, the higher OsBRI1 expression level in the uppermost and fourth internodes does allow these internodes to respond to the brassinosteroid signal and elongate. The higher expression level of OsBRI1 in the uppermost and fourth internodes can explain the unusual internode elongation pattern of the dm-d6 type, but it cannot explain the occurrence of the d6 or dm type. The d6 type, in which all of the internodes except the uppermost are reduced, could indicate that the uppermost internode is exposed to higher levels of brassinosteroids than the fourth internode. The timing of the elongation of the uppermost internode corresponds with the development of anthers in the flowers, and high level of brassinosteroids have been observed in these organs in many plants (Grove, M. et al. (1979) Nature, 281, 216–217; Plattner, D. et al. (1986) J. Natural Products. 49, 540–545; Ikekawa, N. et al. (1988) Chem. Pharm. Bull. 36, 405–407; Takatuto, S. et al. (1989b) Agric. Biol. Chem. 53, 2177–2180; Suzuki, Y. et al. (1986) Agric. Biol. Chem. 50, 3133–3138; Gamoh, K. et al. (1990) Anal. Chim. Acta. 228, 101–105). It appears that high levels of brassinosteroids move down from the anthers to lower organs, such as, the uppermost internode and induce internode elongation and that the fourth internode completes its elongation before flower development and does not receive the high level brassinosteroid signal from the flowers at the time of its active elongation. The brassinosteroid level and the sensitivity to brassinosteroids of OsBRI1 cannot explain the specific retardation of the second internode observed in the dm-type mutants. Therefore, some other factor(s) must be involved. It seems likely that elongation of the second internode is regulated by several factors, since there are several independent dwarf mutants with the dm-phenotype including d1, d2, d11, and d61.

Very recently, the D1 gene was isolated and found to encode a protein with a similar structure to the α subunit (G-α) of a G protein (Fujisawa, Y. et al. (1999) Proc. Natl. Acad. Sci. USA. 96, 7575–7580; Ashikari, M. et al. (1999) Proc. Natl. Acad. Sci. USA. 96, 10284–10289) The D1 G-α like protein is now thought to be involved in the gibberellin (GA) signal transduction pathway, since the d1 mutant alleles show low or no sensitivity to active GA. It is interesting that the loss-of-function mutants of the brassinosteroid signal-related protein, OsBRI1, and that of the GA signal-related protein, Gα, show the same phenotype, i.e., specific retardation of the second internode. Thus, in the induction of elongation in the second internode, there could be a specific mechanism common to brassinosteroids and GA signal transduction in the second internode.

Interestingly, high level expression of OsBRI1 was also seen in the stem at the vegetative stage, in which the internodes do not elongate, showing that high level expression of OsBRI1 in the culm does not necessarily coincide with internode elongation.

EXAMPLE 12

Effect of Exogenous Brassinolide and Light on the Level of OsBRI1 mRNA

The present inventors also tested the effects of exogenously applied brassinolide and light on the level of OsBRI1 mRNA. Germinating seeds were placed on 0.9% agar plates with or without 1 μM brassinolide and grown for six days in the light or dark.

As a result, on plates without brassinosteroids, the expression level of OsBRI1 in dark grown seedlings was higher than in light grown seedlings (FIG. 12D).

This suggests that the dark-grown rice seedlings have a higher sensitivity to brassinosteroids than the light-grown plants (Worley, J. F. and Mitchell, J. W. (1971) J. Amer. Soc. Hort. Sci. 96, 270–273). High sensitivity to brassinosteroids in dark-grown plants will due to the elongation of internode cells in situations where the cells in light-grown plants do not respond to brassinosteroids.

Furthermore, on plates with brassinosteroids, both of the light- and the dark-grown rice seedlings had a reduced level of OsBRI1 expression.

In contrast to rice, the level of BRI1 expression in *Arabidopsis* is little changed between dark- and light-grown seedlings (Li, J. and Chory, J. (1997) Cell. 90, 929–938). The reason for this difference between the expression patterns of the rice OsBRI1 and that of the Arabidopsis BRI1 is not known. However, the difference could be related to the difference in photoresponse mechanisms that rice is short-day plant, while *Arabidopsis* is long-day plant.

EXAMPLE 13

Phenotypic Analysis of Transgenic Plants Expressing the Antisense Strand of OsBRI1

The above phenotypic analyses of the d61 mutants and the single nucleotide exchange in the OsBRI1 genes in each mutant suggest that they might not be null alleles and could retain some partial function. To investigate further the function of brassinosteroids in rice, the present inventors attempted to generate other mutants with more severe phenotypes by overexpression of the antisense strand of the OsBRI1 transcript under the control of the rice Actin1 gene promoter (Zang, W. et al. (1991) Plant Cell. 3, 1155–1165).

For constructing Actin1 promoter::antisense OsBRI1, a promoter-terminator cassette (pBIAct1nos) containing the Act1 promoter (Zhang, W. et al. (1991) Plant Cell. 3, 1155–1165) and NOS terminator was constructed by substitution of the Act1 promoter for the 35S promoter in the hygromycin resistance binary vector, pBI35Snos (Sato, Y. et al. (1999) EMBO J. 18, 992–1002), which contains the 35S promoter and NOS terminator, between the HindIII and XbaI sites. The cDNA clone encoding entire OsBRI1 coding region was introduced between the XbaI and SmaI sites of pBIAct1nos. Vector pBI-cont, containing no insert was used as a control vector. For reduction of OsBRI1 expression, the OsBRI1-antisense cDNA were introduced into the rice cultivar *Nipponbare*. The present inventors performed rice tissue culture and *Agrobacterium tumefaciens* mediated transformation.

Almost all of the resulting transgenic plants (90% or more, 18 out of 20) produced erect leaves during the early stages of seedling growth (FIG. 13D). All of the transformants (20 out of 20) showed a dwarfed phenotype of varying severity (FIG. 13A). In the plants with the weakest phenotype, the length of each internode was partially and uniformly reduced resulting in an elongation pattern similar to that of the wild plant (FIG. 13C) (dn-type mutants). Plants with intermediate phenotypes had the typical internode elongation patterns of dm-type (specific reduction of the second internode, FIG. 13C) or d6-type (specific reduction of the second to fourth internodes, FIG. 13C) mutants or a mixed dm- and d6-type phenotype (specific reduction of the second and third internodes, FIG. 13C). Plants with the severe phenotype only formed abnormal leaves without developed sheath organs and the internodes did not elongate (FIG. 13E). These kinds of plants were less than 15-cm high, even after cultivated for one year or more, and did not produce seeds (FIG. 13B). The other phenotypes were inherited in subsequent generations and cosegregated with hygromycin resistance. The cosegregation between the abnormal phenotypes and hygromycin resistance, and the similarity between the intermediate phenotype of the antisense plants and the d61 mutants demonstrate that the antisense strand acts to suppress the function of OsBRI1 in the transgenic plants.

EXAMPLE 14

Phenotype of Transgenic Plants Expressing Dominant Negative of OsBRI1

Transgenic rice containing the kinase region of the OsBRI1 gene under control of the rice actin 1 gene promoter (Zhang, W. et al., (1991) Plant Cell, 3: 1155–1165) was produced to analyze the function of the rice brassinosteroid receptor. That is, the plasmid was constructed as follows so that only the carboxy terminal kinase domain of brassinosteroid receptor would be expressed without the amino terminus region from the first methionine to 738th glycine. The present inventors used a pair of the primer, 5'-GGCTCTAGACAGCCATGGCGAGCAAGCGGCGGAGGCTG-3'/SEQ ID NO: 4 (5'-primer: which includes TCTAGA as XhoI site, CAGCC added to increase translation efficiency, ATG as the-initiation codon, an additional GCG encoding alanine, and AGC encoding 739th serine, following further nucleotides encoding amino acids after 740th residue of the wild type sequence, lysine, arginine, arginine, and leucine) and 5'-AGATCTACTCCTATAGGTA-3'/SEQ ID NO: 5 (3'-primer: which includes AGATCT as XbaI site and following 3'-untranslated region). These two primers were used to amplify the kinase region of the brassinosteroid receptor. The amplified fragment was then digested with XbaI and inserted into a pBI vector between XbaI-SmaI sites. The vector pBI-cont which does not contain the insert was used as a control.

The rice cultivar Nipponbare was used to produce transgenic plants which expresses kinase domain to control OsBRI1 expression. Rice tissue culture and *Agrobacterium tumefaciens* mediated transformation were performed.

As a result, most of the transgenic plants (90% or more: 25/27 individuals) formed erect leaves at an early stage of seeding growth (FIG. 14). The length between the internodes was partially and equally shortened. The phenotype was inherited to the progeny by co-segregation with hygromycin resistance activity. The co-segregation between the abnormal phenotype and hygromycin resistance and similarities between the dominant negative plants and the d61 mutant intermediate phenotype indicate that the partial cDNA for the kinase portion has activity in the transgenic plant and suppresses OsBRI1 function.

INDUSTRIAL APPLICABILITY

The present invention provides a gene and a protein which functions to increase rice brassinosteroid sensitivity. This gene is involved in elongation of plant internode cells and inclination of leaves. Therefore, it is possible to produce phenotypically modified plants by controlling this gene. For example, by suppressing the expression of the gene of the present invention, dwarf plants, which are resistant to lodging and which enables planting a higher number of individuals per unit area, can be produced, which is significant in the production of crop products. It is also possible to produce ornamental plants having new aesthetic value by dwarfism of height or culm length of said plants via suppression of expression of DNA of the present invention. On the other hand, brassinosteroid sensitivity of the plant can be increased by introducing and expressing the DNA of the present invention in plants, resulting in increase of height of the plant and yield of the whole plant. This is useful especially in increasing yield of plants for animal feed.

The invention claimed is:

1. An isolated DNA being selected from the group consisting of:

(a) DNA encoding a protein comprising the amino acid sequence of SEQ ID NO: 2; and (b) DNA comprising the nucleotide sequence of SEQ ID NO: 1 or 3.

2. The DNA of claim 1, wherein the DNA is cDNA or isolated genomic DNA.

3. The DNA of claim 1, wherein the DNA is derived from a monocotyledonous plant.

4. The DNA of claim 3, wherein the DNA is derived from a plant of the Gramineae family.

5. A vector which comprises the DNA of claim 1.

6. A transformed cell which comprises the DNA of claim 1.

7. A transformed plant, or a progeny, clone, or breeding material thereof, comprising the DNA of claim 1.

8. The isolated DNA of claim 1, wherein the DNA encodes a protein consisting of the amino acid sequence of SEQ ID NO:2.

9. The isolated DNA of claim 1, wherein due DNA comprises SEQ ID NO:1 or 3.

10. The Isolated DNA of claim 1, wherein the DNA consists SEQ ID NO:1 or 3.

* * * * *

UNITED STATES PATENT AND TRADEMARK OFFICE

CERTIFICATE OF CORRECTION

PATENT NO. : 7,135,625 B2
APPLICATION NO. : 10/240577
DATED : November 14, 2006
INVENTOR(S) : Hiroshi Tanaka, Toshiaki Kayano and Makoto Matsuoka It is certified that error appears in the above-identified patent and that said Letters Patent is hereby corrected as shown below:

Column 14,
Line 4, "(lane 3, and" should read --(lane 3), and--.

Column 19,
Line 11, "mutant, 1 kb, does not" should read --mutant, 1kb, does not--.

Column 24,
Line 57, "control vector. For reduction" should read --control vector.
For reduction--.

Column 51,
Line 13, "of the Gramineae family" should read --of the *Gramineae* family--.

Column 52,
Line 8, "wherein due DNA" should read --wherein the DNA--.

Column 52,
Line 10, "The Isolated DNA of" should read --The isolated DNA of--.

Line 11, "consists SEQ ID" should read --consists of SEQ ID--.

Signed and Sealed this

Twenty-first Day of August, 2007

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 3710
<212> TYPE: DNA
<213> ORGANISM: Oryza sativa
<220> FEATURE:
<221> NAME/KEY: misc_feature
<222> LOCATION: (1)..(3710)
<223> OTHER INFORMATION: OsBRI1 cDNA
<220> FEATURE:
<221> NAME/KEY: CDS
<222> LOCATION: (1)..(3363)
<223> OTHER INFORMATION:

<400> SEQUENCE: 1

atg gat tcc ttg tgg gca gcg ata gcg gca ctg ttt gtg gcg gcg gcg       48
Met Asp Ser Leu Trp Ala Ala Ile Ala Ala Leu Phe Val Ala Ala Ala
1               5                   10                  15
```

-continued

```
gtg gtg gtg agg ggg gcg gcg gcg gcc gac gac gcc cag ctg ctc gag       96
Val Val Val Arg Gly Ala Ala Ala Ala Asp Asp Ala Gln Leu Leu Glu
            20                  25                  30

gag ttc agg cag gcg gtg ccg aac cag gcg gcg ctc aag ggg tgg agc      144
Glu Phe Arg Gln Ala Val Pro Asn Gln Ala Ala Leu Lys Gly Trp Ser
        35                  40                  45

ggc ggc gac ggc gcg tgc agg ttc ccg ggg gcc ggg tgc cgg aac ggg      192
Gly Gly Asp Gly Ala Cys Arg Phe Pro Gly Ala Gly Cys Arg Asn Gly
    50                  55                  60

agg ctc acg tcg ctg tcg ctc gcc ggc gtg ccg ctc aat gcc gag ttc      240
Arg Leu Thr Ser Leu Ser Leu Ala Gly Val Pro Leu Asn Ala Glu Phe
65                  70                  75                  80

cgc gcc gtc gcg gcc acc ctg ctg cag ctc ggc agc gtc gag gtg ctg      288
Arg Ala Val Ala Ala Thr Leu Leu Gln Leu Gly Ser Val Glu Val Leu
                85                  90                  95

agc ctc cgc ggc gcc aac gtc agc ggc gcg ctc tcg gcg gct ggc ggc      336
Ser Leu Arg Gly Ala Asn Val Ser Gly Ala Leu Ser Ala Ala Gly Gly
            100                 105                 110

gcg agg tgc ggg agc aag ctg cag gcg ctc gat ttg tcc ggg aat gcc      384
Ala Arg Cys Gly Ser Lys Leu Gln Ala Leu Asp Leu Ser Gly Asn Ala
        115                 120                 125

gcg ctc cgg ggc tcc gtc gcc gac gtg gcg gcc ctg gcc agc gcc tgc      432
Ala Leu Arg Gly Ser Val Ala Asp Val Ala Ala Leu Ala Ser Ala Cys
    130                 135                 140

ggc ggc ctc aag acg ctg aat ctc tcc ggc gat gcg gtt ggt gcg gcg      480
Gly Gly Leu Lys Thr Leu Asn Leu Ser Gly Asp Ala Val Gly Ala Ala
145                 150                 155                 160

aag gtc ggt ggc ggt ggt ggc ccg ggc ttt gcc ggg ctg gac tcg ctt      528
Lys Val Gly Gly Gly Gly Gly Pro Gly Phe Ala Gly Leu Asp Ser Leu
                165                 170                 175

gat ttg tcc aac aac aag atc acc gac gat agc gac ctc cgg tgg atg      576
Asp Leu Ser Asn Asn Lys Ile Thr Asp Asp Ser Asp Leu Arg Trp Met
            180                 185                 190

gtg gat gcc gga gtc ggg gca gta cgg tgg ttg gac ctt gcc ctg aac      624
Val Asp Ala Gly Val Gly Ala Val Arg Trp Leu Asp Leu Ala Leu Asn
        195                 200                 205

agg atc tcc ggt gtc ccg gag ttc acc aac tgc tcc ggg ctt cag tac      672
Arg Ile Ser Gly Val Pro Glu Phe Thr Asn Cys Ser Gly Leu Gln Tyr
    210                 215                 220

ctt gac ctc tcc ggc aac ctc atc gtc ggt gag gtg ccc ggc ggg gca      720
Leu Asp Leu Ser Gly Asn Leu Ile Val Gly Glu Val Pro Gly Gly Ala
225                 230                 235                 240

ctt tcc gac tgc cgc ggt ctg aaa gtg ctc aac ctc tcc ttc aac cac      768
Leu Ser Asp Cys Arg Gly Leu Lys Val Leu Asn Leu Ser Phe Asn His
                245                 250                 255

ctc gcc ggc gtg ttc cct ccg gac atc gcc ggc ctc acg tcg ctc aac      816
Leu Ala Gly Val Phe Pro Pro Asp Ile Ala Gly Leu Thr Ser Leu Asn
            260                 265                 270

gcc ctc aac ctc tcc aac aac aac ttc tcc ggc gag ctc ccc ggc gag      864
Ala Leu Asn Leu Ser Asn Asn Asn Phe Ser Gly Glu Leu Pro Gly Glu
        275                 280                 285

gct ttc gca aag ctg cag cag ctt acg gcg ctc tcc ctc tcc ttc aac      912
Ala Phe Ala Lys Leu Gln Gln Leu Thr Ala Leu Ser Leu Ser Phe Asn
    290                 295                 300

cac ttc aac ggc tcc atc ccg gac acc gta gcc tcg ctg ccg gag ctc      960
His Phe Asn Gly Ser Ile Pro Asp Thr Val Ala Ser Leu Pro Glu Leu
305                 310                 315                 320

cag cag ctc gac ctc agc tcc aac acc ttc tcc ggc acc atc ccg tcg     1008
Gln Gln Leu Asp Leu Ser Ser Asn Thr Phe Ser Gly Thr Ile Pro Ser
                325                 330                 335
```

-continued

```
tcc ctc tgc caa gat ccc aac tcc aag ctc cat ctg ctg tac ctt cag      1056
Ser Leu Cys Gln Asp Pro Asn Ser Lys Leu His Leu Leu Tyr Leu Gln
            340                 345                 350

aac aac tac ctc acc ggc ggc atc cca gac gcc gtc tcc aac tgc acc      1104
Asn Asn Tyr Leu Thr Gly Gly Ile Pro Asp Ala Val Ser Asn Cys Thr
        355                 360                 365

agc ctc gtc tcc ctc gac ctc agc ctc aac tac atc aat ggg tcc atc      1152
Ser Leu Val Ser Leu Asp Leu Ser Leu Asn Tyr Ile Asn Gly Ser Ile
    370                 375                 380

ccg gca tcc ctc ggc gac ctt ggc aac ctg cag gac ctc atc ctg tgg      1200
Pro Ala Ser Leu Gly Asp Leu Gly Asn Leu Gln Asp Leu Ile Leu Trp
385                 390                 395                 400

cag aac gag ctg gag ggc gag ata ccg gcg tcc ctg tcg cgc att cag      1248
Gln Asn Glu Leu Glu Gly Glu Ile Pro Ala Ser Leu Ser Arg Ile Gln
                405                 410                 415

ggc ctc gag cat ctc atc ctc gac tac aac ggg ctc acg ggt agc atc      1296
Gly Leu Glu His Leu Ile Leu Asp Tyr Asn Gly Leu Thr Gly Ser Ile
            420                 425                 430

ccg ccg gag cta gcc aag tgc acc aag ctg aac tgg att tct ttg gcg      1344
Pro Pro Glu Leu Ala Lys Cys Thr Lys Leu Asn Trp Ile Ser Leu Ala
        435                 440                 445

agc aac cgg ctg tcc ggg cca atc cct tca tgg ctt ggg aag ctc agc      1392
Ser Asn Arg Leu Ser Gly Pro Ile Pro Ser Trp Leu Gly Lys Leu Ser
    450                 455                 460

tac ttg gct atc ttg aag ctc agc aac aat tcc ttc tcg ggg cct ata      1440
Tyr Leu Ala Ile Leu Lys Leu Ser Asn Asn Ser Phe Ser Gly Pro Ile
465                 470                 475                 480

ccg cca gag ctc ggt gac tgc cag agc ttg gtg tgg ctg gac ctg aat      1488
Pro Pro Glu Leu Gly Asp Cys Gln Ser Leu Val Trp Leu Asp Leu Asn
                485                 490                 495

agc aat cag ctg aat gga tca ata ccc aaa gag ctg gcc aaa cag tct      1536
Ser Asn Gln Leu Asn Gly Ser Ile Pro Lys Glu Leu Ala Lys Gln Ser
            500                 505                 510

ggg aag atg aat gtt ggc ctc ata gtt gga cgg cct tac gtt tat ctt      1584
Gly Lys Met Asn Val Gly Leu Ile Val Gly Arg Pro Tyr Val Tyr Leu
        515                 520                 525

cgc aac gac gag ctg agc agc gag tgc cgt ggc aag ggg agc ttg ctg      1632
Arg Asn Asp Glu Leu Ser Ser Glu Cys Arg Gly Lys Gly Ser Leu Leu
    530                 535                 540

gag ttt acc agc atc cga cct gat gac ctc agt cgg atg ccg agc aag      1680
Glu Phe Thr Ser Ile Arg Pro Asp Asp Leu Ser Arg Met Pro Ser Lys
545                 550                 555                 560

aag ctg tgc aac ttc aca aga atg tat gtg ggg agc acg gag tac acc      1728
Lys Leu Cys Asn Phe Thr Arg Met Tyr Val Gly Ser Thr Glu Tyr Thr
                565                 570                 575

ttc aac aag aat ggt tcg atg ata ttt ctc gat ttg tca tat aat cag      1776
Phe Asn Lys Asn Gly Ser Met Ile Phe Leu Asp Leu Ser Tyr Asn Gln
            580                 585                 590

ctg gac tcg gcg att cct ggc gag ctg ggg gac atg ttc tac ctc atg      1824
Leu Asp Ser Ala Ile Pro Gly Glu Leu Gly Asp Met Phe Tyr Leu Met
        595                 600                 605

atc atg aat ctt ggg cac aac cta ctg tca ggt acc atc cca tcg cgg      1872
Ile Met Asn Leu Gly His Asn Leu Leu Ser Gly Thr Ile Pro Ser Arg
    610                 615                 620

cta gca gag gcc aag aag ctt gcg gtg ctt gac ctg tcg tat aac cag      1920
Leu Ala Glu Ala Lys Lys Leu Ala Val Leu Asp Leu Ser Tyr Asn Gln
625                 630                 635                 640

ttg gaa ggg cca ata ccc aac tct ttc tcg gca ctt tcc ttg tcg gag      1968
Leu Glu Gly Pro Ile Pro Asn Ser Phe Ser Ala Leu Ser Leu Ser Glu
```

-continued

```
            645                 650                 655

atc aat ctg tca aat aat cag ctg aat gga aca att cca gag ctt ggt     2016
Ile Asn Leu Ser Asn Asn Gln Leu Asn Gly Thr Ile Pro Glu Leu Gly
        660                 665                 670

tcc ctt gcc aca ttt ccg aag agc cag tat gag aat aac act ggt tta     2064
Ser Leu Ala Thr Phe Pro Lys Ser Gln Tyr Glu Asn Asn Thr Gly Leu
    675                 680                 685

tgt ggc ttc cca ctg cca cca tgt gac cat agt tcc cca aga tct tcc     2112
Cys Gly Phe Pro Leu Pro Pro Cys Asp His Ser Ser Pro Arg Ser Ser
    690                 695                 700

aat gac cac caa tcc cac cgg agg cag gca tcg atg gca agc agt atc     2160
Asn Asp His Gln Ser His Arg Arg Gln Ala Ser Met Ala Ser Ser Ile
705                 710                 715                 720

gct atg gga ctg tta ttc tca ctg ttc tgt ata att gtg atc atc ata     2208
Ala Met Gly Leu Leu Phe Ser Leu Phe Cys Ile Ile Val Ile Ile Ile
            725                 730                 735

gcc att ggg agc aag cgg cgg agg ctg aag aat gag gag gcg agt acc     2256
Ala Ile Gly Ser Lys Arg Arg Arg Leu Lys Asn Glu Glu Ala Ser Thr
        740                 745                 750

tct cgt gat ata tat att gat agc agg tca cat tct gca act atg aat     2304
Ser Arg Asp Ile Tyr Ile Asp Ser Arg Ser His Ser Ala Thr Met Asn
    755                 760                 765

tct gat tgg agg caa aat ctc tcc ggt aca aat ctt ctt agc atc aac     2352
Ser Asp Trp Arg Gln Asn Leu Ser Gly Thr Asn Leu Leu Ser Ile Asn
    770                 775                 780

ctg gct gca ttc gag aag cca ttg cag aat ctc acc ctg gct gat ctt     2400
Leu Ala Ala Phe Glu Lys Pro Leu Gln Asn Leu Thr Leu Ala Asp Leu
785                 790                 795                 800

gtt gag gcc aca aat ggc ttc cac atc gca tgc caa att ggg tct ggt     2448
Val Glu Ala Thr Asn Gly Phe His Ile Ala Cys Gln Ile Gly Ser Gly
            805                 810                 815

ggg ttt ggt gat gtc tac aag gca cag ctc aag gat ggg aag gtt gtt     2496
Gly Phe Gly Asp Val Tyr Lys Ala Gln Leu Lys Asp Gly Lys Val Val
        820                 825                 830

gca atc aag aag cta ata cat gtg agc ggg cag ggt gac cgg gag ttc     2544
Ala Ile Lys Lys Leu Ile His Val Ser Gly Gln Gly Asp Arg Glu Phe
    835                 840                 845

act gca gaa atg gag acc att ggc aag atc aaa cac cgt aac ctt gtt     2592
Thr Ala Glu Met Glu Thr Ile Gly Lys Ile Lys His Arg Asn Leu Val
    850                 855                 860

cca ctt ctt ggc tat tgc aag gct ggt gag gag cgg ttg ttg gtg tat     2640
Pro Leu Leu Gly Tyr Cys Lys Ala Gly Glu Glu Arg Leu Leu Val Tyr
865                 870                 875                 880

gat tac atg aag ttt ggc agc ttg gag gat gtg ttg cat gac cgc aaa     2688
Asp Tyr Met Lys Phe Gly Ser Leu Glu Asp Val Leu His Asp Arg Lys
            885                 890                 895

aag atc ggt aaa aag ctg aat tgg gag gca aga cgg aaa atc gct gtt     2736
Lys Ile Gly Lys Lys Leu Asn Trp Glu Ala Arg Arg Lys Ile Ala Val
        900                 905                 910

gga gca gca agg ggt ttg gca ttc ctc cac cac aat tgc att cct cac     2784
Gly Ala Ala Arg Gly Leu Ala Phe Leu His His Asn Cys Ile Pro His
    915                 920                 925

atc att cac cga gac atg aag tcg agc aat gtg ctt atc gat gaa caa     2832
Ile Ile His Arg Asp Met Lys Ser Ser Asn Val Leu Ile Asp Glu Gln
    930                 935                 940

ctg gaa gca agg gta tct gat ttc ggt atg gcg agg ctg atg agc gtg     2880
Leu Glu Ala Arg Val Ser Asp Phe Gly Met Ala Arg Leu Met Ser Val
945                 950                 955                 960

gtg gat aca cac ctt agc gtg tcc act ctt gct gga acg cca ggg tat     2928
```

-continued

```
Val Asp Thr His Leu Ser Val Ser Thr Leu Ala Gly Thr Pro Gly Tyr
                965                 970                 975

gta cca ccg gag tac tac cag agc ttc aga tgc acc acc aag ggt gat     2976
Val Pro Pro Glu Tyr Tyr Gln Ser Phe Arg Cys Thr Thr Lys Gly Asp
            980                 985                 990

gtt tat agc tat ggt gtt gtg ttg  ctg gag ctg ctc acc  ggg aaa ccg   3024
Val Tyr Ser Tyr Gly Val Val Leu  Leu Glu Leu Leu Thr  Gly Lys Pro
        995                 1000                1005

ccg acg  gac tcg gca gac ttt  ggc gag gac aat aac  ctt gtg ggg      3069
Pro Thr  Asp Ser Ala Asp Phe  Gly Glu Asp Asn Asn  Leu Val Gly
    1010                1015                1020

tgg gtc  aag cag cac acc aaa  ttg aag atc acg gat  gtc ttc gac      3114
Trp Val  Lys Gln His Thr Lys  Leu Lys Ile Thr Asp  Val Phe Asp
    1025                1030                1035

cct gag  cta ctc aag gag gat  cca tcc gtc gag ctt  gag ctg ctg      3159
Pro Glu  Leu Leu Lys Glu Asp  Pro Ser Val Glu Leu  Glu Leu Leu
    1040                1045                1050

gag cat  ttg aaa atc gcc tgt  gcg tgc ttg gat gac  cgg ccg tcg      3204
Glu His  Leu Lys Ile Ala Cys  Ala Cys Leu Asp Asp  Arg Pro Ser
    1055                1060                1065

agg cgg  ccg acg atg ctg aag  gtg atg gca atg ttc  aag gag atc      3249
Arg Arg  Pro Thr Met Leu Lys  Val Met Ala Met Phe  Lys Glu Ile
    1070                1075                1080

caa gct  ggg tcg acg gtc gac  tcg aag acc tcg tcg  gcg gca gcg      3294
Gln Ala  Gly Ser Thr Val Asp  Ser Lys Thr Ser Ser  Ala Ala Ala
    1085                1090                1095

ggc tcg  atc gat gag gga ggc  tat ggg gtc ctt gac  atg ccc ctc      3339
Gly Ser  Ile Asp Glu Gly Gly  Tyr Gly Val Leu Asp  Met Pro Leu
    1100                1105                1110

agg gaa  gcc aag gag gag aag  gat tagaaacaac aaccaccgac            3383
Arg Glu  Ala Lys Glu Glu Lys  Asp
    1115                1120

acacaggaga aacagccggc ggtgagtggc caccaacgag gccagtcggc ggcgaaatgc   3443

ccgtagaaac aacagtcatt cagaatcaga tggatgccat tttgaactct ccacacaagc   3503

ttagcaatcg cttctgatgg tgctacaaga taagaatttt ccagctgtag gttgatcagt   3563

cgaagttgtt atgtacctat aggagtagat cttttcttct ttcttttttc gcagctttct   3623

tcgtctccct gtttgttttt cccgtcgcgt cgcagtaaga gctgtgtatg tacatatata   3683

aatgttgaat tttctttggc gcaaaat                                       3710


<210> SEQ ID NO 2
<211> LENGTH: 1121
<212> TYPE: PRT
<213> ORGANISM: Oryza sativa
<220> FEATURE:
<221> NAME/KEY: MISC_FEATURE
<222> LOCATION: (1)..(1121)
<223> OTHER INFORMATION: BRI1 protein (Genbank Accession BAB68053)

<400> SEQUENCE: 2

Met Asp Ser Leu Trp Ala Ala Ile Ala Ala Leu Phe Val Ala Ala Ala
1               5                   10                  15

Val Val Val Arg Gly Ala Ala Ala Ala Asp Asp Ala Gln Leu Leu Glu
            20                  25                  30

Glu Phe Arg Gln Ala Val Pro Asn Gln Ala Ala Leu Lys Gly Trp Ser
        35                  40                  45

Gly Gly Asp Gly Ala Cys Arg Phe Pro Gly Ala Gly Cys Arg Asn Gly
    50                  55                  60
```

-continued

```
Arg Leu Thr Ser Leu Ser Leu Ala Gly Val Pro Leu Asn Ala Glu Phe
65                  70                  75                  80

Arg Ala Val Ala Ala Thr Leu Leu Gln Leu Gly Ser Val Glu Val Leu
                85                  90                  95

Ser Leu Arg Gly Ala Asn Val Ser Gly Ala Leu Ser Ala Ala Gly Gly
            100                 105                 110

Ala Arg Cys Gly Ser Lys Leu Gln Ala Leu Asp Leu Ser Gly Asn Ala
        115                 120                 125

Ala Leu Arg Gly Ser Val Ala Asp Val Ala Ala Leu Ala Ser Ala Cys
    130                 135                 140

Gly Gly Leu Lys Thr Leu Asn Leu Ser Gly Asp Ala Val Gly Ala Ala
145                 150                 155                 160

Lys Val Gly Gly Gly Gly Gly Pro Gly Phe Ala Gly Leu Asp Ser Leu
                165                 170                 175

Asp Leu Ser Asn Asn Lys Ile Thr Asp Asp Ser Asp Leu Arg Trp Met
            180                 185                 190

Val Asp Ala Gly Val Gly Ala Val Arg Trp Leu Asp Leu Ala Leu Asn
        195                 200                 205

Arg Ile Ser Gly Val Pro Glu Phe Thr Asn Cys Ser Gly Leu Gln Tyr
    210                 215                 220

Leu Asp Leu Ser Gly Asn Leu Ile Val Gly Glu Val Pro Gly Gly Ala
225                 230                 235                 240

Leu Ser Asp Cys Arg Gly Leu Lys Val Leu Asn Leu Ser Phe Asn His
                245                 250                 255

Leu Ala Gly Val Phe Pro Pro Asp Ile Ala Gly Leu Thr Ser Leu Asn
            260                 265                 270

Ala Leu Asn Leu Ser Asn Asn Asn Phe Ser Gly Glu Leu Pro Gly Glu
        275                 280                 285

Ala Phe Ala Lys Leu Gln Gln Leu Thr Ala Leu Ser Leu Ser Phe Asn
    290                 295                 300

His Phe Asn Gly Ser Ile Pro Asp Thr Val Ala Ser Leu Pro Glu Leu
305                 310                 315                 320

Gln Gln Leu Asp Leu Ser Ser Asn Thr Phe Ser Gly Thr Ile Pro Ser
                325                 330                 335

Ser Leu Cys Gln Asp Pro Asn Ser Lys Leu His Leu Leu Tyr Leu Gln
            340                 345                 350

Asn Asn Tyr Leu Thr Gly Gly Ile Pro Asp Ala Val Ser Asn Cys Thr
        355                 360                 365

Ser Leu Val Ser Leu Asp Leu Ser Leu Asn Tyr Ile Asn Gly Ser Ile
    370                 375                 380

Pro Ala Ser Leu Gly Asp Leu Gly Asn Leu Gln Asp Leu Ile Leu Trp
385                 390                 395                 400

Gln Asn Glu Leu Glu Gly Glu Ile Pro Ala Ser Leu Ser Arg Ile Gln
                405                 410                 415

Gly Leu Glu His Leu Ile Leu Asp Tyr Asn Gly Leu Thr Gly Ser Ile
            420                 425                 430

Pro Pro Glu Leu Ala Lys Cys Thr Lys Leu Asn Trp Ile Ser Leu Ala
        435                 440                 445

Ser Asn Arg Leu Ser Gly Pro Ile Pro Ser Trp Leu Gly Lys Leu Ser
    450                 455                 460

Tyr Leu Ala Ile Leu Lys Leu Ser Asn Asn Ser Phe Ser Gly Pro Ile
465                 470                 475                 480

Pro Pro Glu Leu Gly Asp Cys Gln Ser Leu Val Trp Leu Asp Leu Asn
```

-continued

```
                485                 490                 495

Ser Asn Gln Leu Asn Gly Ser Ile Pro Lys Glu Leu Ala Lys Gln Ser
            500                 505                 510

Gly Lys Met Asn Val Gly Leu Ile Val Gly Arg Pro Tyr Val Tyr Leu
        515                 520                 525

Arg Asn Asp Glu Leu Ser Ser Glu Cys Arg Gly Lys Gly Ser Leu Leu
    530                 535                 540

Glu Phe Thr Ser Ile Arg Pro Asp Asp Leu Ser Arg Met Pro Ser Lys
545                 550                 555                 560

Lys Leu Cys Asn Phe Thr Arg Met Tyr Val Gly Ser Thr Glu Tyr Thr
                565                 570                 575

Phe Asn Lys Asn Gly Ser Met Ile Phe Leu Asp Leu Ser Tyr Asn Gln
            580                 585                 590

Leu Asp Ser Ala Ile Pro Gly Glu Leu Gly Asp Met Phe Tyr Leu Met
        595                 600                 605

Ile Met Asn Leu Gly His Asn Leu Leu Ser Gly Thr Ile Pro Ser Arg
    610                 615                 620

Leu Ala Glu Ala Lys Lys Leu Ala Val Leu Asp Leu Ser Tyr Asn Gln
625                 630                 635                 640

Leu Glu Gly Pro Ile Pro Asn Ser Phe Ser Ala Leu Ser Leu Ser Glu
                645                 650                 655

Ile Asn Leu Ser Asn Asn Gln Leu Asn Gly Thr Ile Pro Glu Leu Gly
            660                 665                 670

Ser Leu Ala Thr Phe Pro Lys Ser Gln Tyr Glu Asn Asn Thr Gly Leu
        675                 680                 685

Cys Gly Phe Pro Leu Pro Pro Cys Asp His Ser Ser Pro Arg Ser Ser
    690                 695                 700

Asn Asp His Gln Ser His Arg Arg Gln Ala Ser Met Ala Ser Ser Ile
705                 710                 715                 720

Ala Met Gly Leu Leu Phe Ser Leu Phe Cys Ile Ile Val Ile Ile Ile
                725                 730                 735

Ala Ile Gly Ser Lys Arg Arg Arg Leu Lys Asn Glu Glu Ala Ser Thr
            740                 745                 750

Ser Arg Asp Ile Tyr Ile Asp Ser Arg Ser His Ser Ala Thr Met Asn
        755                 760                 765

Ser Asp Trp Arg Gln Asn Leu Ser Gly Thr Asn Leu Leu Ser Ile Asn
    770                 775                 780

Leu Ala Ala Phe Glu Lys Pro Leu Gln Asn Leu Thr Leu Ala Asp Leu
785                 790                 795                 800

Val Glu Ala Thr Asn Gly Phe His Ile Ala Cys Gln Ile Gly Ser Gly
                805                 810                 815

Gly Phe Gly Asp Val Tyr Lys Ala Gln Leu Lys Asp Gly Lys Val Val
            820                 825                 830

Ala Ile Lys Lys Leu Ile His Val Ser Gly Gln Gly Asp Arg Glu Phe
        835                 840                 845

Thr Ala Glu Met Glu Thr Ile Gly Lys Ile Lys His Arg Asn Leu Val
    850                 855                 860

Pro Leu Leu Gly Tyr Cys Lys Ala Gly Glu Glu Arg Leu Leu Val Tyr
865                 870                 875                 880

Asp Tyr Met Lys Phe Gly Ser Leu Glu Asp Val Leu His Asp Arg Lys
                885                 890                 895

Lys Ile Gly Lys Lys Leu Asn Trp Glu Ala Arg Arg Lys Ile Ala Val
            900                 905                 910
```

-continued

```
Gly Ala Ala Arg Gly Leu Ala Phe Leu His His Asn Cys Ile Pro His
        915                 920                 925

Ile Ile His Arg Asp Met Lys Ser Ser Asn Val Leu Ile Asp Glu Gln
    930                 935                 940

Leu Glu Ala Arg Val Ser Asp Phe Gly Met Ala Arg Leu Met Ser Val
945                 950                 955                 960

Val Asp Thr His Leu Ser Val Ser Thr Leu Ala Gly Thr Pro Gly Tyr
                965                 970                 975

Val Pro Pro Glu Tyr Tyr Gln Ser Phe Arg Cys Thr Thr Lys Gly Asp
            980                 985                 990

Val Tyr Ser Tyr Gly Val Val Leu  Leu Glu Leu Leu Thr  Gly Lys Pro
        995                 1000                1005

Pro Thr  Asp Ser Ala Asp Phe  Gly Glu Asp Asn Asn  Leu Val Gly
    1010                 1015                1020

Trp Val  Lys Gln His Thr Lys  Leu Lys Ile Thr Asp  Val Phe Asp
    1025                 1030                1035

Pro Glu  Leu Leu Lys Glu Asp  Pro Ser Val Glu Leu  Glu Leu Leu
    1040                 1045                1050

Glu His  Leu Lys Ile Ala Cys  Ala Cys Leu Asp Asp  Arg Pro Ser
    1055                 1060                1065

Arg Arg  Pro Thr Met Leu Lys  Val Met Ala Met Phe  Lys Glu Ile
    1070                 1075                1080

Gln Ala  Gly Ser Thr Val Asp  Ser Lys Thr Ser Ser  Ala Ala Ala
    1085                 1090                1095

Gly Ser  Ile Asp Glu Gly Gly  Tyr Gly Val Leu Asp  Met Pro Leu
    1100                 1105                1110

Arg Glu  Ala Lys Glu Glu Lys  Asp
    1115                 1120
```

```
<210> SEQ ID NO 3
<211> LENGTH: 4538
<212> TYPE: DNA
<213> ORGANISM: Oryza sativa
<220> FEATURE:
<221> NAME/KEY: misc_feature
<222> LOCATION: (1)..(4538)
<223> OTHER INFORMATION: OsBRI1 genomic DNA

<400> SEQUENCE: 3

ctcgagcaga ccaccggctg tccccggccg tcggatcgga tcgggattta acctcgccgt     60

aagccgcgga taagcgcggg ggattagaat acttaacctc tcctctgctc tcctcctcac    120

ccggcttaag cgcgcggggg ggctgcgatt cgcaggcgag agcacatgcc atgtgacccc    180

accccaccac tcctccctca cctacagctg ttaaggccag tcacaatggg ggtttcactg    240

gtgtgtcatg cacatttaat aggggtaaga ctgaataaaa aatgattatt tgcatgaaat    300

ggggatgaga gagaaggaaa gagtttcatc ctggtgaaac tcgtcagcgt cgtttccaag    360

tcctcggtaa cagagtgaaa cccccgttga ggccgattcg tttcattcac cggatctctt    420

gcgtccgcct ccgccgtgcg acctccgcat tctcccgcgc cgcgccggat tttgggtaca    480

aatgatccca gcaacttgta tcaattaaat gctttgctta gtcttggaaa cgtcaaagtg    540

aaacccctcc actgtgggga ttgtttcata aaagatttca tttgagagaa gatggtataa    600

tattttgggt agccgtgcaa tgacactagc cattgtgact ggcctaattg ctctccccct    660

ctactgtgtt tgcgtctttc ttcttcgctt ctctttctct ctctctccat ctcctcctca    720
```

-continued

```
tcacttccca ctctcccccct tctgtctctc tactttctct ctctaccgcc gctctcgcag     780
caggccaggt tctctctaat ggtcgtgagg cagtgagctc gctcgtacat ggattccttg     840
tgggcagcga tagcggcact gtttgtggcg gcggcggtgg tggtgagggg ggcggcggcg     900
gccgacgacg cccagctgct cgaggagttc aggcaggcgg tgccgaacca ggcggcgctc     960
aaggggtgga gcggcggcga cggcgcgtgc aggttcccgg gggccgggtg ccggaacggg    1020
aggctcacgt cgctgtcgct cgccggcgtg ccgctcaatg ccgagttccg cgccgtcgcg    1080
gccaccctgc tgcagctcgg cagcgtcgag gtgctgagcc tccgcggcgc caacgtcagc    1140
ggcgcgctct cggcggctgg cggcgcgagg tgcgggagca agctgcaggc gctcgatttg    1200
tccgggaatg ccgcgctccg gggctccgtc gccgacgtgg cggccctggc cagcgcctgc    1260
ggcggcctca agacgctgaa tctctccggc gatgcggttg gtgcggcgaa ggtcggtggc    1320
ggtggtggcc cgggctttgc cgggctggac tcgcttgatt tgtccaacaa caagatcacc    1380
gacgatagcg acctccggtg gatggtggat gccggagtcg ggcagtacgg gtggttggac    1440
cttgccctga acaggatctc cggtgtcccg gagttcacca actgctccgg gcttcagtac    1500
cttgacctct ccggcaacct catcgtcggt gaggtgcccg gcggggcact ttccgactgc    1560
cgcggtctga aagtgctcaa cctctccttc aaccacctcg ccggcgtgtt ccctccggac    1620
atcgccggcc tcacgtcgct caacgccctc aacctctcca acaacaactt ctccggcgag    1680
ctccccggcg aggctttcgc aaagctgcag cagcttacgg cgctctccct ctccttcaac    1740
cacttcaacg gctccatccc ggacaccgta gcctcgctgc cggagctcca gcagctcgac    1800
ctcagctcca acaccttctc cggcaccatc ccgtcgtccc tctgccaaga tcccaactcc    1860
aagctccatc tgctgtacct tcagaacaac tacctcaccg gcggcatccc agacgccgtc    1920
tccaactgca ccagcctcgt ctccctcgac ctcagcctca actacatcaa tgggtccatc    1980
ccggcatccc tcggcgacct tggcaacctg caggacctca tcctgtggca gaacgagctg    2040
gagggcgaga taccggcgtc cctgtcgcgc attcagggcc tcgagcatct catcctcgac    2100
tacaacgggc tcacgggtag catcccgccg gagctagcca agtgcaccaa gctgaactgg    2160
atttctttgg cgagcaaccg gctgtccggg ccaatccctt catggcttgg gaagctcagc    2220
tacttggcta tcttgaagct cagcaacaat tccttctcgg ggcctatacc gccagagctc    2280
ggtgactgcc agagcttggt gtggctggac ctgaatagca atcagctgaa tggatcaata    2340
cccaaagagc tggccaaaca gtctgggaag atgaatgttg gcctcatagt tggacggcct    2400
tacgtttatc ttcgcaacga cgagctgagc agcgagtgcc gtggcaaggg gagcttgctg    2460
gagtttacca gcatccgacc tgatgacctc agtcggatgc cgagcaagaa gctgtgcaac    2520
ttcacaagaa tgtatgtggg gagcacggag tacaccttca acaagaatgg ttcgatgata    2580
tttctcgatt tgtcatataa tcagctggac tcggcgattc ctggcgagct gggggacatg    2640
ttctacctca tgatcatgaa tcttgggcac aacctactgt caggtaccat cccatcgcgg    2700
ctagcagagg ccaagaagct tgcggtgctt gacctgtcgt ataaccagtt ggaagggcca    2760
atacccaact ctttctcggc actttccttg tcggagatca atctgtcaaa taatcagctg    2820
aatggaacaa ttccagagct tggttccctt gccacatttc cgaagagcca gtatgagaat    2880
aacactggtt tatgtggctt cccactgcca ccatgtgacc atagttcccc aagatcttcc    2940
aatgaccacc aatcccaccg gaggcaggca tcgatggcaa gcagtatcgc tatgggactg    3000
ttattctcac tgttctgtat aattgtgatc atcatagcca ttgggagcaa gcggcggagg    3060
ctgaagaatg aggaggcgag tacctctcgt gatatatata ttgatagcag gtcacattct    3120
```

gcaactatga attctgattg gaggcaaaat ctctccggta caaatcttct tagcatcaac 3180
ctggctgcat tcgagaagcc attgcagaat ctcaccctgg ctgatcttgt tgaggccaca 3240
aatggcttcc acatcgcatg ccaaattggg tctggtgggt ttggtgatgt ctacaaggca 3300
cagctcaagg atgggaaggt tgttgcaatc aagaagctaa tacatgtgag cgggcagggt 3360
gaccgggagt tcactgcaga aatggagacc attggcaaga tcaaacaccg taaccttgtt 3420
ccacttcttg gctattgcaa ggctggtgag gagcggttgt tggtgtatga ttacatgaag 3480
tttggcagct tggaggatgt gttgcatgac cgcaaaaaga tcggtaaaaa gctgaattgg 3540
gaggcaagac ggaaaatcgc tgttggagca gcaaggggtt tggcattcct ccaccacaat 3600
tgcattcctc acatcattca ccgagacatg aagtcgagca atgtgcttat cgatgaacaa 3660
ctggaagcaa gggtatctga tttcggtatg gcgaggctga tgagcgtggt ggatacacac 3720
cttagcgtgt ccactcttgc tggaacgcca gggtatgtac caccggagta ctaccagagc 3780
ttcagatgca ccaccaaggg tgatgtttat agctatggtg ttgtgttgct ggagctgctc 3840
accgggaaac cgccgacgga ctcggcagac tttggcgagg acaataacct tgtggggtgg 3900
gtcaagcagc acaccaaatt gaagatcacg gatgtcttcg accctgagct actcaaggag 3960
gatccatccg tcgagcttga gctgctggag catttgaaaa tcgcctgtgc gtgcttggat 4020
gaccggccgt cgaggcggcc gacgatgctg aaggtgatgg caatgttcaa ggagatccaa 4080
gctgggtcga cggtcgactc gaagacctcg tcggcggcag cgggctcgat cgatgaggga 4140
ggctatgggg tccttgacat gcccctcagg gaagccaagg aggagaagga ttagaaacaa 4200
caaccaccga cacacaggag aaacagccgg cggtgagtgg ccaccaacga ggccagtcgg 4260
cggcgaaatg cccgtagaaa caacagtcat tcagaatcag atggatgcca ttttgaactc 4320
tccacacaag cttagcaatc gcttctgatg gtgctacaag ataagaattt tccagctgta 4380
ggttgatcag tcgaagttgt tatgtaccta taggagtaga tcttttcttc tttctttttt 4440
cgcagctttc ttcgtctccc tgtttgtttt tcccgtcgcg tcgcagtaag agctgtgtat 4500
gtacatatat aaatgttgaa ttttctttgg cgcaaaat 4538

<210> SEQ ID NO 4
<211> LENGTH: 38
<212> TYPE: DNA
<213> ORGANISM: Artificial Sequence
<220> FEATURE:
<223> OTHER INFORMATION: 5' primer sequence

<400> SEQUENCE: 4
ggctctagac agccatggcg agcaagcggc ggaggctg 38

<210> SEQ ID NO 5
<211> LENGTH: 19
<212> TYPE: DNA
<213> ORGANISM: Artificial Sequence
<220> FEATURE:
<223> OTHER INFORMATION: 3' primer sequence

<400> SEQUENCE: 5
agatctactc ctataggta 19

<210> SEQ ID NO 6
<211> LENGTH: 1196
<212> TYPE: PRT
<213> ORGANISM: Arabidopsis thaliana
<220> FEATURE:

-continued

```
<221> NAME/KEY: MISC_FEATURE
<222> LOCATION: (1)..(1196)
<223> OTHER INFORMATION: BRI1 protein (Genbank Accession NP_195650)

<400> SEQUENCE: 6

Met Lys Thr Phe Ser Ser Phe Phe Leu Ser Val Thr Thr Leu Phe Phe
1               5                   10                  15

Phe Ser Phe Phe Ser Leu Ser Phe Gln Ala Ser Pro Ser Gln Ser Leu
            20                  25                  30

Tyr Arg Glu Ile His Gln Leu Ile Ser Phe Lys Asp Val Leu Pro Asp
        35                  40                  45

Lys Asn Leu Leu Pro Asp Trp Ser Ser Asn Lys Asn Pro Cys Thr Phe
    50                  55                  60

Asp Gly Val Thr Cys Arg Asp Asp Lys Val Thr Ser Ile Asp Leu Ser
65                  70                  75                  80

Ser Lys Pro Leu Asn Val Gly Phe Ser Ala Val Ser Ser Ser Leu Leu
                85                  90                  95

Ser Leu Thr Gly Leu Glu Ser Leu Phe Leu Ser Asn Ser His Ile Asn
            100                 105                 110

Gly Ser Val Ser Gly Phe Lys Cys Ser Ala Ser Leu Thr Ser Leu Asp
        115                 120                 125

Leu Ser Arg Asn Ser Leu Ser Gly Pro Val Thr Thr Leu Thr Ser Leu
    130                 135                 140

Gly Ser Cys Ser Gly Leu Lys Phe Leu Asn Val Ser Ser Asn Thr Leu
145                 150                 155                 160

Asp Phe Pro Gly Lys Val Ser Gly Gly Leu Lys Leu Asn Ser Leu Glu
                165                 170                 175

Val Leu Asp Leu Ser Ala Asn Ser Ile Ser Gly Ala Asn Val Val Gly
            180                 185                 190

Trp Val Leu Ser Asp Gly Cys Gly Glu Leu Lys His Leu Ala Ile Ser
        195                 200                 205

Gly Asn Lys Ile Ser Gly Asp Val Asp Val Ser Arg Cys Val Asn Leu
    210                 215                 220

Glu Phe Leu Asp Val Ser Ser Asn Asn Phe Ser Thr Gly Ile Pro Phe
225                 230                 235                 240

Leu Gly Asp Cys Ser Ala Leu Gln His Leu Asp Ile Ser Gly Asn Lys
                245                 250                 255

Leu Ser Gly Asp Phe Ser Arg Ala Ile Ser Thr Cys Thr Glu Leu Lys
            260                 265                 270

Leu Leu Asn Ile Ser Ser Asn Gln Phe Val Gly Pro Ile Pro Pro Leu
        275                 280                 285

Pro Leu Lys Ser Leu Gln Tyr Leu Ser Leu Ala Glu Asn Lys Phe Thr
    290                 295                 300

Gly Glu Ile Pro Asp Phe Leu Ser Gly Ala Cys Asp Thr Leu Thr Gly
305                 310                 315                 320

Leu Asp Leu Ser Gly Asn His Phe Tyr Gly Ala Val Pro Pro Phe Phe
                325                 330                 335

Gly Ser Cys Ser Leu Leu Glu Ser Leu Ala Leu Ser Ser Asn Asn Phe
            340                 345                 350

Ser Gly Glu Leu Pro Met Asp Thr Leu Leu Lys Met Arg Gly Leu Lys
        355                 360                 365

Val Leu Asp Leu Ser Phe Asn Glu Phe Ser Gly Glu Leu Pro Glu Ser
    370                 375                 380

Leu Thr Asn Leu Ser Ala Ser Leu Leu Thr Leu Asp Leu Ser Ser Asn
```

-continued

```
385                 390                 395                 400

Asn Phe Ser Gly Pro Ile Leu Pro Asn Leu Cys Gln Asn Pro Lys Asn
                405                 410                 415

Thr Leu Gln Glu Leu Tyr Leu Gln Asn Asn Gly Phe Thr Gly Lys Ile
            420                 425                 430

Pro Pro Thr Leu Ser Asn Cys Ser Glu Leu Val Ser Leu His Leu Ser
        435                 440                 445

Phe Asn Tyr Leu Ser Gly Thr Ile Pro Ser Ser Leu Gly Ser Leu Ser
    450                 455                 460

Lys Leu Arg Asp Leu Lys Leu Trp Leu Asn Met Leu Glu Gly Glu Ile
465                 470                 475                 480

Pro Gln Glu Leu Met Tyr Val Lys Thr Leu Glu Thr Leu Ile Leu Asp
                485                 490                 495

Phe Asn Asp Leu Thr Gly Glu Ile Pro Ser Gly Leu Ser Asn Cys Thr
            500                 505                 510

Asn Leu Asn Trp Ile Ser Leu Ser Asn Asn Arg Leu Thr Gly Glu Ile
        515                 520                 525

Pro Lys Trp Ile Gly Arg Leu Glu Asn Leu Ala Ile Leu Lys Leu Ser
    530                 535                 540

Asn Asn Ser Phe Ser Gly Asn Ile Pro Ala Glu Leu Gly Asp Cys Arg
545                 550                 555                 560

Ser Leu Ile Trp Leu Asp Leu Asn Thr Asn Leu Phe Asn Gly Thr Ile
                565                 570                 575

Pro Ala Ala Met Phe Lys Gln Ser Gly Lys Ile Ala Ala Asn Phe Ile
            580                 585                 590

Ala Gly Lys Arg Tyr Val Tyr Ile Lys Asn Asp Gly Met Lys Lys Glu
        595                 600                 605

Cys His Gly Ala Gly Asn Leu Leu Glu Phe Gln Gly Ile Arg Ser Glu
    610                 615                 620

Gln Leu Asn Arg Leu Ser Thr Arg Asn Pro Cys Asn Ile Thr Ser Arg
625                 630                 635                 640

Val Tyr Gly Gly His Thr Ser Pro Thr Phe Asp Asn Asn Gly Ser Met
                645                 650                 655

Met Phe Leu Asp Met Ser Tyr Asn Met Leu Ser Gly Tyr Ile Pro Lys
            660                 665                 670

Glu Ile Gly Ser Met Pro Tyr Leu Phe Ile Leu Asn Leu Gly His Asn
        675                 680                 685

Asp Ile Ser Gly Ser Ile Pro Asp Glu Val Gly Asp Leu Arg Gly Leu
    690                 695                 700

Asn Ile Leu Asp Leu Ser Ser Asn Lys Leu Asp Gly Arg Ile Pro Gln
705                 710                 715                 720

Ala Met Ser Ala Leu Thr Met Leu Thr Glu Ile Asp Leu Ser Asn Asn
                725                 730                 735

Asn Leu Ser Gly Pro Ile Pro Glu Met Gly Gln Phe Glu Thr Phe Pro
            740                 745                 750

Pro Ala Lys Phe Leu Asn Asn Pro Gly Leu Cys Gly Tyr Pro Leu Pro
        755                 760                 765

Arg Cys Asp Pro Ser Asn Ala Asp Gly Tyr Ala His His Gln Arg Ser
    770                 775                 780

His Gly Arg Arg Pro Ala Ser Leu Ala Gly Ser Val Ala Met Gly Leu
785                 790                 795                 800

Leu Phe Ser Phe Val Cys Ile Phe Gly Leu Ile Leu Val Gly Arg Glu
                805                 810                 815
```

-continued

```
Met Arg Lys Arg Arg Arg Lys Lys Glu Ala Glu Leu Glu Met Tyr Ala
            820                 825                 830

Glu Gly His Gly Asn Ser Gly Asp Arg Thr Ala Asn Asn Thr Asn Trp
        835                 840                 845

Lys Leu Thr Gly Val Lys Glu Ala Leu Ser Ile Asn Leu Ala Ala Phe
    850                 855                 860

Glu Lys Pro Leu Arg Lys Leu Thr Phe Ala Asp Leu Leu Gln Ala Thr
865                 870                 875                 880

Asn Gly Phe His Asn Asp Ser Leu Ile Gly Ser Gly Gly Phe Gly Asp
                885                 890                 895

Val Tyr Lys Ala Ile Leu Lys Asp Gly Ser Ala Val Ala Ile Lys Lys
            900                 905                 910

Leu Ile His Val Ser Gly Gln Gly Asp Arg Glu Phe Met Ala Glu Met
        915                 920                 925

Glu Thr Ile Gly Lys Ile Lys His Arg Asn Leu Val Pro Leu Leu Gly
    930                 935                 940

Tyr Cys Lys Val Gly Asp Glu Arg Leu Leu Val Tyr Glu Phe Met Lys
945                 950                 955                 960

Tyr Gly Ser Leu Glu Asp Val Leu His Asp Pro Lys Lys Ala Gly Val
                965                 970                 975

Lys Leu Asn Trp Ser Thr Arg Arg Lys Ile Ala Ile Gly Ser Ala Arg
            980                 985                 990

Gly Leu Ala Phe Leu His His Asn  Cys Ser Pro His Ile  Ile His Arg
        995                 1000                1005

Asp Met  Lys Ser Ser Asn Val  Leu Leu Asp Glu Asn  Leu Glu Ala
    1010                 1015                 1020

Arg Val  Ser Asp Phe Gly Met  Ala Arg Leu Met Ser  Ala Met Asp
    1025                 1030                 1035

Thr His  Leu Ser Val Ser Thr  Leu Ala Gly Thr Pro  Gly Tyr Val
    1040                 1045                 1050

Pro Pro  Glu Tyr Tyr Gln Ser  Phe Arg Cys Ser Thr  Lys Gly Asp
    1055                 1060                 1065

Val Tyr  Ser Tyr Gly Val Val  Leu Leu Glu Leu Leu  Thr Gly Lys
    1070                 1075                 1080

Arg Pro  Thr Asp Ser Pro Asp  Phe Gly Asp Asn Asn  Leu Val Gly
    1085                 1090                 1095

Trp Val  Lys Gln His Ala Lys  Leu Arg Ile Ser Asp  Val Phe Asp
    1100                 1105                 1110

Pro Glu  Leu Met Lys Glu Asp  Pro Ala Leu Glu Ile  Glu Leu Leu
    1115                 1120                 1125

Gln His  Leu Lys Val Ala Val  Ala Cys Leu Asp Asp  Arg Ala Trp
    1130                 1135                 1140

Arg Arg  Pro Thr Met Val Gln  Val Met Ala Met Phe  Lys Glu Ile
    1145                 1150                 1155

Gln Ala  Gly Ser Gly Ile Asp  Ser Gln Ser Thr Ile  Arg Ser Ile
    1160                 1165                 1170

Glu Asp  Gly Gly Phe Ser Thr  Ile Glu Met Val Asp  Met Ser Ile
    1175                 1180                 1185

Lys Glu  Val Pro Glu Gly Lys  Leu
    1190                 1195
```